(12) United States Patent
Wong et al.

(10) Patent No.: US 6,423,834 B1
(45) Date of Patent: Jul. 23, 2002

(54) KDO ALDOLASE AND CONDENSATION REACTIONS EMPLOYED THEREWITH

(75) Inventors: Chi-Huey Wong, Rancho Santa Fe, CA (US); Takeshi Sugai, Yokohama (JP); Gwo-Jenn Shen, Carlsbad, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/247,164

(22) Filed: Feb. 9, 1999

Related U.S. Application Data

(62) Division of application No. 08/767,182, filed on Dec. 16, 1996, now Pat. No. 5,869,315, which is a division of application No. 08/328,739, filed on Oct. 25, 1994, now Pat. No. 5,585,261, which is a division of application No. 07/993,140, filed on Dec. 18, 1992, now Pat. No. 5,358,859.

(51) Int. Cl.$^7$ ............................................. C07H 15/00

(52) U.S. Cl. ..................... 536/18.6; 536/1.11; 536/115; 536/124

(58) Field of Search .............................. 536/1.11, 18.6, 536/124, 115

(56) References Cited

U.S. PATENT DOCUMENTS

| | | |
|---|---|---|
| 5,162,513 A | 11/1992 | Wong et al. |
| 5,358,859 A | 10/1994 | Wong et al. |
| 5,585,261 A | 12/1996 | Wong et al. |
| 5,759,825 A | 6/1998 | Wong et al. |
| 5,869,316 A | 2/1999 | Wong et al. |

OTHER PUBLICATIONS

Ghalambor, et al., "The Chemical Synthesis of 2–Keto–3–deoxy–octonate and its Cleavage by a Specific Aldolase", *Biochem. Biophys. Res. Commun.* 11: 288–293 (1963).

Madson, et al., "The Oxidation of 3–Deoxy–D–erythro–hexos–2–ulose ("3–Deoxyglucosone") to 3–Deoxy–D–erythro–2–hexulosonic acid ("2–Keto–3–deoxy–D–gluconate") by D–Glucose Oxidase", *Carbohyd. Res.* 115: 288–291 (1983).

Sengupta, et al., "Structural Analogs of 2–Keto–3–deoxy–D–mannooctulosonic Acid", *Ind. J. Chem. Sect. B 25B*: 85–87 (1986).

Augé, et al., "Sialyl Aldolase in Organic Synthesis: From the Trout Egg Acid, 3–Deoxy–D–Glycero–D–Galacto–2–Nonulosonic Acid (KDN), to Branched–Chain Higher Ketoses as Possible New Chirons.", *Tetrahedron* 46: 201–214 (1990).

Knappmann, et al., "Localization of the enzyme 3–Deoxy–D–Manno–2–Octulosonic Acid Aldolase", *Appl. Microbiol. Biotechnol.* 33: 324–329 (1990).

Auzanneau, et al., "Formation of methyl (2,7–anhydro–3–deoxy–α–D–manno–2–octulofuranos)onate upon methanolysis of 2,4,7, 8–tetra–O–acetyl–3–deoxy–α–D–manno–2–octulopyranosono–1,5–lactone", *Carbohyd. Res.* 201: 337–241 (1990).

Drueckhammer, et al., "Enzyme Catalysis in Synthetic Carbohydrate Chemistry", *Synthesis:* 499–525 (1991).

Ramage, et al., "Dioxalanones as Synthetic Intermediates. Part 6. Synthesis of 3–Deoxy–D–manno–2–octulosonic acid (KDO), 3–Deoxy–D–arabino–2–heptulsonic acid (DAH) and 2–Keto–3–deoxy–D–gluconic acid (KDG)", *Tetrahedron* 47: 5625–5636 (1991).

Becker, et al., "2–Keto–Sugar Acids in Green Flagellates: A Chemical Marker for Prasinophycean Scales", *J. Phycol.* 27: 498–504 (1991).

Sugai, et al., "Synthesis of 3–Deoxy–D–manno–2–octulosonic Acid (KDO) and its Analogs Based on KDO Aldolase–Catalyzed Reactions", *J. Am. Chem. Soc.* 115: 413–421 (1993).

Sugai, et al., "Improved Enzymatic Procedure for a Preparative–Scale Synthesis of Sialic Acid and KDN", *Bull. Chem. Soc. Jpn.* 68: 3581–3589 (1995).

Haverkamp, et al., "High–Resolution N–NMR Spectroscopy of Free and Glycosidically Linked 0–Acetylated Sialic Acids", *Eur. J. Biochem.*, 122:305–311 (1982).

*Primary Examiner*—Gary Geist
*Assistant Examiner*—Howard V. Owens, Jr.
(74) *Attorney, Agent, or Firm*—Donald G. Lewis; Thomas Fitting

(57) ABSTRACT

*Aureobacterium barkerei* strain KDO-37-2 (ATCC 49977) and KDO aldolase (EC 4.1.2.23) isolated therefrom are disclosed. The KDO aldolase is further disclosed to have a broad substrate specificity with respect to its reverse reaction, i.e. the condensation of aldoses with pyruvate to form a wide range of 2-keto-3-deoxy-onic acids, including 2-keto-3-deoxy-nonulosonic acid, 2-keto-3-deoxy-octulosonic acid, 2-keto-3-deoxy-heptulosonic acid, and 2-keto-3-deoxy-hexulosonic acid. In particular, 3-deoxy-D-manno-2-octulosonic acid (D-KDO), a vital component of lipopolysaccharides found in the bacterial outer membrane may be synthesized from D-arabinose and pyruvate in 67% yield. Additionally, protected forms of the KDO aldolase products, e.g. hexaacetyl 2-keto-3-deoxy-nonulosonic acid and pentaacetyl 2-keto-3-deoxy-octulosonic acid, may be decarboxylated to form the corresponding 2-deoxy-aldoses, e.g. 2-deoxy-octulose and 2-deoxy-heptulose respectively.

5 Claims, 16 Drawing Sheets

Good substrates

D-threose

D-erythrose

D-arabinose

D-ribose 2-deoxy-
D-ribose

Fair substrates

L-glyceraldehyde

D-glyceraldehyde 2-deoxy-2-fluoro-
D-arabinose

D-lyxose 5-azido-2,5-
dideoxy-D-ribose

D-altrose

L-mannose $^1$H NMR spectrum of 6, the product from 2-deoxy-D-ribose (400 MHz, $CDCl_3$)

L-mannose

L-KDN: 15

16

$[\alpha]_D$ +26.3° (CHCl$_3$)

23a

23b

KDO ALDOLASE AND CONDENSATION REACTIONS EMPLOYED THEREWITH

CROSS-REFERENCE TO RELATED APPLICATION

This is a divisional application of application Ser. No. 08/767,182, filed Dec. 16, 1996, issued Feb. 9, 1999 as U.S. Pat. No. 5,869,316, which is a divisional application of application Ser. No. 08/328,739, filed Oct. 25, 1994, issued Dec. 17, 1996 as U.S. Pat. No. 5,585,261, which is a divisional application of application Ser. No. 07/993,140, filed Dec. 18, 1992, issued Oct. 25, 1994 as U.S. Pat. No. 5,358,859.

GOVERNMENT RIGHTS

This invention was made with government support under Grant No. GM 44154 awarded by the National Institutes of Health. The U.S. government has certain rights in the invention.

DESCRIPTION

Technical Field

The invention relates to KDO aldolase (EC 4.1.2.23) having a broad substrate specificity with respect to its reverse reaction and to condensation reactions employing such KDO aldolase for synthesizing a broad range of 6–9 carbon 2-keto-3-deoxy-onic acids, viz. 2-keto-3-deoxy-hexulosonate, 2-keto-3-deoxy-heptulosonate, 2-keto-3-deoxy-octulosonate, and 2-keto-3-deoxy-nonulosonate. More particularly, the invention relates to *Aureobacterium barkerei* strain KDO-37-2 (ATCC 49977), to KDO aldolase produced by and isolated from such bacteria, to the employment of such KDO aldose with respect to the synthesis of 2-keto-3-deoxy-onic acids such as 3-deoxy-D-manno-2-octulosonic acid (D-KDO) and to the use of protected forms of such 2-keto-3-deoxy-onic acids for the production of 7 and 8 carbon aldoses by means of radical mediated decarboxylation.

BACKGROUND OF THE INVENTION

2-Keto-3-deoxy-octulosonic acid (KDO) appears as a ketosidic component of all Gram-negative bacteria for which a KDO determination has been made. More particularly, 3-deoxy-D-manno-2-octulosonic acid (D-KDO) is widely found in Gram-negative bacteria. KDO is incorporated into lipopolysaccharides and is localized, as such, within the outer membrane compartment of Gram-negative bacteria. KDO appears to be a vital component of Gram-negative bacteria. KDO can also occur as an acidic exopolysaccharide. In such instances, the KDO can serve as part of a K-antigen.

As illustrated in FIG. 7, the biosynthetic incorporation of KDO into lipopolysaccharides consists of two steps, i.e.:

1. Activation of KDO to form CMP-KDO by means of CMP-KDO synthetase (EC 2.7.7.38); and then
2. Coupling of the activated CMP-KDO to lipid A precursor to form lipid A-KDO by means of KDO transferase.

The rate-limiting step with respect to the biosynthesis of KDO containing lipopolysaccharides is the activation of the KDO moiety, i.e., the formation of CMP-KDO. Accordingly, inhibitors of CMP-KDO synthetase are potentially useful as antibacterial agents.

Several chemical and enzymatic synthetic routes have been developed for the synthesis of KDO and its analogs. One route for the chemical synthesis of KDO employs Cornforth's method. (Ghalambor, M. et al. *J. Biol. Chem.* 1966, 241, 3207 and Hershberger, C. et al. *J. Biol. Chem.* 1968, 243, 1585.) The chemical synthesis of KDO produces multiple enantiomers. In order to obtain enantiomerically pure D-KDO, a separation step must be incorporated into the chemical synthetic route.

Synthetic routes employing enzymes are more stereospecific than chemical synthetic routes. An enzymatic synthetic route employing KDO-8 phosphate synthase and KDO-8-P phosphatase as catalysts and arabinose-5-P and PEP as substrates is illustrated in FIG. 7. (Bednarski, M. et al. *Tetrahedron Letters* 1988, 29, 427.) An alternative enzymatic synthetic route employs sialic acid aldolase. (Augé, C. et al. *Tetrahedron* 1990, 46, 201.)

An enzymatic synthetic route employing the reverse reaction of KDO aldolase for a micromolar scale synthesis of KDO is disclosed by Ghalambor. (Ghalambor, M. et al., *J. Biol. Chem.* 1966, 241, 3222.) The synthetic route described by Ghalambor employs KDO aldolase isolated from *Aerobacter cloacae*. The reverse reaction of KDO aldolase is driven by employing high substrate levels, i.e. high concentrations of D-arabinose and D-pyruvate. Ghalambor discloses that there is a 41% yield with this enzyme and narrow substrate specificity.

KDO aldolase (EC 4.1.2.23) is known to be inductively produced by several bacteria, viz. *Escherichia coli*, strains 0111, B, and K-12, *Salmonella typhimurium, Salmonella aldelaide*, and *Aerobacter cloacae*. Ghalambor discloses that all of these known KDO aldolases have comparable activities. For example, all of these KDO aldolases hydrolyze 3-deoxy-D-manno-2-octulosonic acid to form D-arabinose and pyruvate in a forward reaction. As indicated above, Ghalambor also discloses that known KDO aldolase may be employed in a reverse reaction to condense D-arabinose and pyruvate to form 3-deoxy-D-manno-2-octulosonic acid. The substrate specificity of known KDO aldolases with respect to this reverse reaction is confined to D-arabinose and has been specifically shown to lack a measurable specificity for D-ribose in connection with this reverse reaction.

What was needed was an enzymic synthetic route for the production of a wide range of 2-keto-3-deoxy-onic acids and analogs thereof potentially having activity as inhibitors of CMP-KDO synthetase.

What was also needed was a method of converting 2-keto-3-deoxy-onic acids to high-carbon 2-deoxy aldoses.

SUMMARY OF THE INVENTION

*Aureobacterium barkerei* strain KDO-37-2 (ATCC 49977) and KDO aldolase (EC 4.1.2.23) isolated therefrom are disclosed therein. KDO aldolase catalyzed condensation employing this enzyme has been demonstrated to be effective for the synthesis of KDO and analogs. The reactions are stereospecific with formation of a new R-stereocenter at C-3 from D-arabinose and related substrates. Decarboxylation of the aldolase products provides a new route to heptose and octose derivatives.

Unlike known KDO aldolases which have a narrow substrate specificity, the KDO aldolase isolated from this source is disclosed to have a very wide substrate specificity with respect to catalyzing its reverse reaction, i.e. the condensation of aldoses with pyruvate. In particular, 3-deoxy-D-manno-2-octulosonic acid (D-KDO) can be synthesized from D-arabinose and pyruvate in 67% yield. Furthermore, studies with respect to the substrate specificity of the enzyme using more than 20 natural and unnatural sugars indicate that this enzyme widely accepts trioses, tetroses, pentoses and hexoses as substrates, especially the ones with R configuration at 3 position. The substituent on 2 position has little effect on the aldol reaction. Nine of these substrates are submitted to the aldol reaction to prepare various 2-keto-3-deoxy-onic acids, including D-KDO, 3-deoxy-D-arabino-2-heptulosonic acid (D-DAH), 2-keto-3-deoxy-L-gluconic acid (L-KDG), and 3-deoxy-L-glycero-L-galacto-nonulosonic acid (L-KDN). The attack of pyruvate appears to take place on the re face of the carbonyl group of acceptor substrates, a facial selection complementary to sialic acid aldolase (si face attack) reactions. The aldolase products can be converted to aldoses via radical-mediated decarboxylation. For example, decarboxylation of pentaacetyl KDO and hexaacetyl neuraminic acid gives penta-O-acetyl-2-deoxy-β,3-D-manno-heptose and penta-O-acetyl-4-acetamido-2,4-dideoxy-β-D-glycero-D-gala cto-octose, respectively.

BRIEF DESCRIPTION OF DRAWINGS

FIG. 8A illustrates a synthetic scheme employing KDO aldolase and D-arabinose.

FIG. 8B illustrates a synthetic scheme employing KDO aldolase and D-ribose.

FIG. 8C illustrates a synthetic scheme employing KDO aldolase and 2-deoxy-D-ribose.

FIG. 8D illustrates a synthetic scheme employing KDO aldolase and D-erythrose.

FIG. 8E illustrates a synthetic scheme employing KDO aldolase and D-glyceraldehyde.

FIG. 8F illustrates a synthetic scheme employing KDO aldolase and D-threose.

FIG. 8G illustrates a synthetic scheme employing KDO aldolase and L-glyceraldehyde.

FIG. 8H illustrates a synthetic scheme employing KDO aldolase and L-mannose.

FIG. 8I illustrates a synthetic scheme employing sialic acid aldolase and D-mannose.

Additionally, FIG. 9A illustrates the stabilization of a planar conformer of the radical intermediate, stabilized both by the electron-donating and withdrawing effects, thereby allowing the maximum interaction between the one-electron p orbital and the lone pair electrons on the adjacent ring oxygen.

DETAILED DESCRIPTION

A New Source of KDO Aldolase

*Aureobacterium barkerei* strain KDO-37-2 (ATCC 49977) was isolated from garden soil using KDO as a major carbon source. The microorganism (strain KDO-37-2) grows well on LB medium. It is aerobic, gram-positive, not motile and with colonies 1–3 millimeters in diameter on LB agar plates. The colony morphology is circular, low convex, entire edge and produces yellow pigment. Optimum growth temperature is about 30° C. Major fatty acids are anteiso-$C_{15:0}$ and anteiso-$C_{17:0}$. The strain was identified as *Aureobacterium barkerei* according to Bergey's manual. A deposit of *Aureobacterium barkerei* strain KDO-37-2 was made Jul. 30, 1992 with the American Type Culture Collection (ATCC) 12301 Parklawn Drive, Rockville, Md., USA 20852 and was given Accession Number ATCC 49977.

The deposit with accession Number ATCC 49977 was made in compliance with the Budapest Treaty requirements that the duration of the deposits should be for 30 years from the date of deposit at the depository or for the enforceable life of a U.S. patent that matures from this application, whichever is longer. The cell line will be replenished should it become non-viable at the depository.

A preferred medium for KDO aldolase production is defined as follows: $NH_4Cl$ (5 grams), $K_2SO_4$ (1 gram), $MgSO_4 \cdot 7H_2O$ (200 milligrams), $CaCl_2$ (20 milligrams), $FeSO_4 \cdot 7H_2O$ (1 milligram), yeast extract (1 gram), $Na_2HPO_4 \cdot 7H_2O$ and $KH_2PO_4$ (3 grams) in distilled water (1 liter) at pH 7.2. A seed culture may be made by admixing in a 100 milliliter Erlenmeyer flask 50 milliliters of the above medium together with 25 microliters of a 40% glucose solution and 100 milligrams (0.2%) of KDO. The seed culture is then inoculated with a loopful of *Aureobacterium barkerei* strain KDO-37-2 (ATCC 49977). The flask is then shaken at 250 r.p.m. on a gyrorotory shaker at 30° C. for 16 hours. The seed culture thus obtained may then be poured into the 1950 milliliters of the same medium containing LDO as a major carbon source. The culture was incubated for 24 hours at 30° C. with shaking. The cells may be harvested as a source of KDO aldolase enzyme.

For routine culture preservation, the culture can grow on LB medium and can be incubated overnight at 30° C. This strain of *Aureobacterium barkerei* is shown to be a source of KDO aldolase (EC 4.1.2.23) having a broad substrate specificity with respect to the reverse aldol condensation reaction.

A New Source of KDO Aldolase

Figure 7:
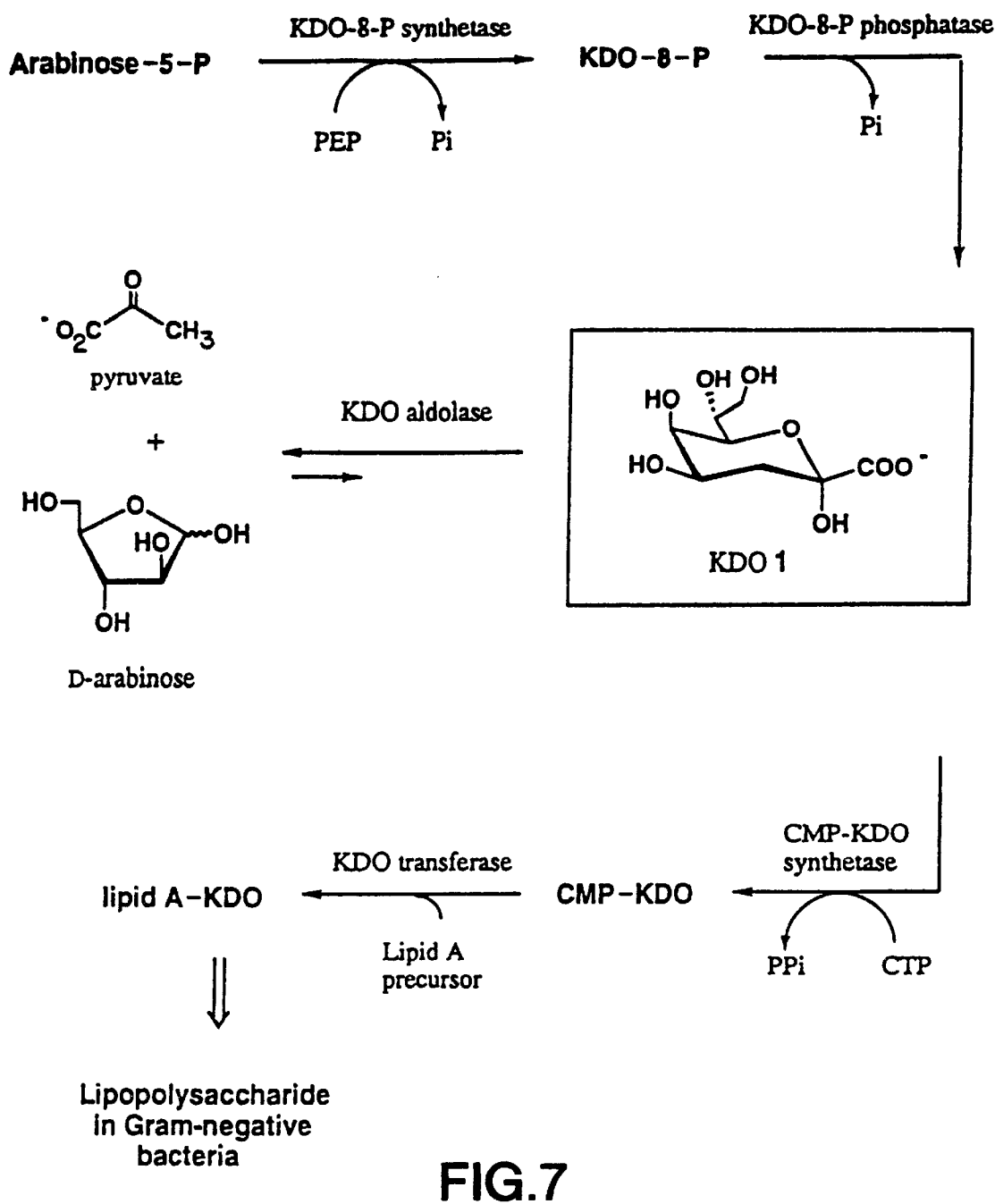
FIG. 7 illustrates a prior art biosynthetic incorporation of KDO into lipopolysaccharides and a prior art enzymatic synthetic route employing KDO-8 phosphate synthase and KDO-8-P phosphatase as catalysts and arabinose-5-P and PEP as substrates.

KDO aldolase (EC 4.1.2.23) was first reported by Ghalambor and Heath in 1966 as the enzyme responsible for the KDO degradation (FIG. 7). After their preliminary investigation on the substrate specificity as well as the μmol scale synthesis of KDO, no synthetic application of this enzyme has been reported, while the related enzyme N-acetylneuraminic acid (sialic acid) aldolase has been extensively studied.

It is disclosed herein that the Gram-positive bacterium *Aureobacterium barkerei* strain KDO-37-2 can be induced to contain high levels of KDO aldolase. The aldolase activity from this source was assayed according to Aminoff's method (*Biochem. J.* 1961, 81, 384). Two liters of culture contained 10.2 U based on the degradation of KDO. This KDO activity is 4 times and 8 times higher than the corresponding KDO activity from *Escherichia coli* K-12 and *Aerobacter cloacae*, respectively, as reported by Gharambor (supra).

Partially purified KDO aldolase simply obtained by ammonium sulfate precipitation (8.0 U/mL; 0.19 U/mg for degradation of KDO) was used in substrate-specificity studies reported herein. The KDO aldolase employed for the kinetic analysis reported herein, was further purified via DEAE sepharose and phenyl sepharose column chromatography to a specific activity of 5.7 U/mg. The $K_m$ for D-arabinose and $V_{max}$ are 1.2 M and 0.73 U/mg, respectively. The unusually high concentration of $K_m$ in the condensation compared with that in the course of degradation ($6 \times 10^{-3}$ M for KDO) indicates that the enzyme may accept the open form of aldoses as acceptors in the aldol condensation. The enzymatic reaction favors the cleavage of KDO, with the equilibrium constant $K_{eq}$=[pyruvate][arabinose]/KDO=$9 \times 10^{-2}$M.

Substrate Specificity

Figure 1:
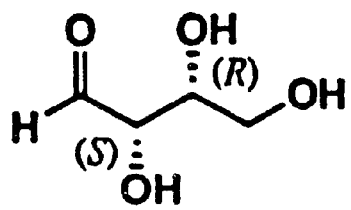
FIG. 1 illustrates saccharides having good specificity for KDO aldolase isolated from *Aureobacterium barkerei* KDO-37-2.
Figure 1:
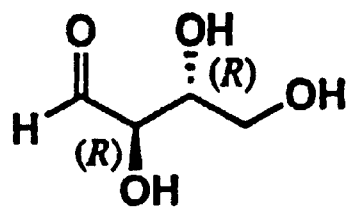
Figure 1:
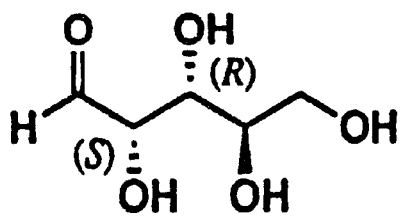
Figure 1:
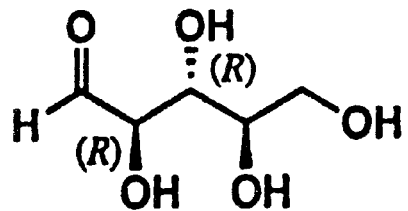
Figure 1:
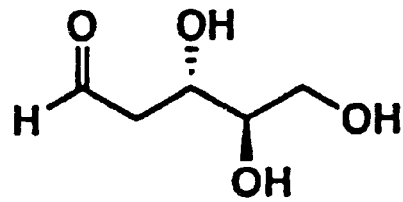

This enzyme exhibits a wide substrate specificity. Several 3–6 carbon sugars were accepted as substrates for the condensation. From the results shown in Table I and FIG. 1, the structural requirements of the sugar for this enzyme are as follows. At C-2 position, although the aldolase prefers an S configuration, the difference is not significant [examples: between L- and D-glyceraldehyde; D-threose and D-erythrose; D-arabinose, D-ribose and 2-deoxy-D-ribose]. It is noteworthy that this enzyme also accepts D-ribose as a good substrate (rel. V=72%), while that from *E. coli* or *Aerobacter cloacae* poorly accepts this substrate (rel. V<5%), according to Gharambor (supra). At C-3 position, this enzyme prefers an R-configuration [examples: comparison between D-arabinose and L-arabinose, D-lyxose and D-xylose]. Hexoses are generally not as good substrates as tetroses and pentoses, even in the case of D-altrose (rel. V=25%) and L-fucose (rate not detectable), both being homoanalogs of the natural substrate D-arabinose. The reason that L-mannose is a better substrate than D-mannose is because the former has the favorable 2R,3R configurations and the latter has the unfavorable 2S,3S configurations. Finally, neither fluoropyruvate nor ketohexose was accepted by this enzyme.

The Aldol Condensation

Figure 8A:
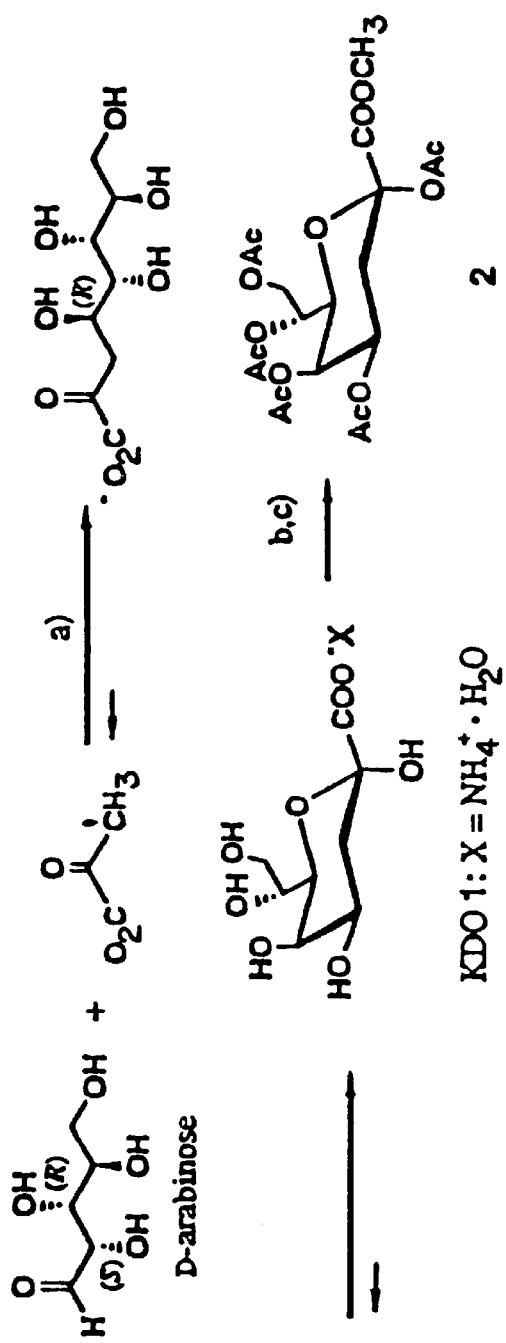
FIGS. 8A–I illustrate a synthetic scheme employing an aldolase condensation reaction and an excess of pyruvate for producing KDO from a variety of starting sugars.

The enzymatic synthesis of KDO on multi-mmol scales using 10 molar excess of pyruvate worked well (e.g. 1 was obtained in 67% yield). The synthetic route is illustrated in FIG. 8A. The reagents employed in this synthesis are as follows:

| Step | Reagent or Enzyme |
|---|---|
| (a) | KDO aldolase |
| (b) | $Ac_2O$/py, DMAP |
| (c) | $CH_2N_2$. |

The yield of the enzymatic reaction is comparable to the highest one obtained by the modified Cornforth synthesis (66%). The crystalline KDO ammonium salt monohydrate was isolated in 37% yield: $[\alpha]^{26}D$ +40.3° (c 2.06, $H_2O$) [lit. according to Unger: $[\alpha]^{27}D$ +42.3° (c, 1.7, $H_2O$), authentic sample from Sigma $[\alpha]^{26}D$ +40.2° (c 2.06, $H_2O$)]. (Unger: Adv. Carbohydr. Chem. Biochem. 1981, 38, 323.) The $^1$H NMR spectrum in $D_2O$ is identical with that of an authentic sample, although it is complicated by the fact that KDO exists as an anomeric mixture of pyranose and furanose forms, and readily cyclizes to the corresponding lactone in aqueous solution. The crystalline ammonium salt was further converted to pentaacetate methyl ester derivative 2, whose $^1$H NMR spectrum was in good accordance with that reported previously and clearly shows the $^5C_2$-pyranose conformation (Table II).

Figure 2:
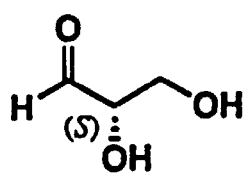
FIG. 2 illustrates saccharides having fair specificity for KDO aldolase isolated from *Aureobacterium barkerei* KDO-37-2.
Figure 2:
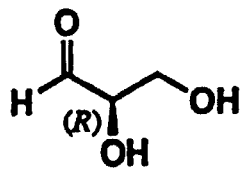
Figure 2:
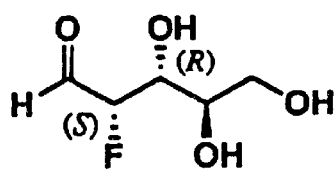
Figure 2:
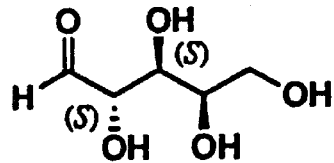
Figure 2:
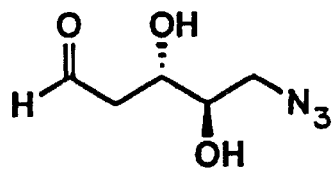
Figure 2:
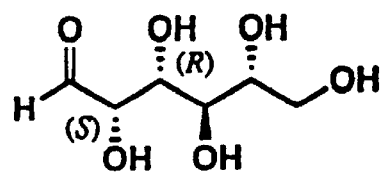
Figure 2:
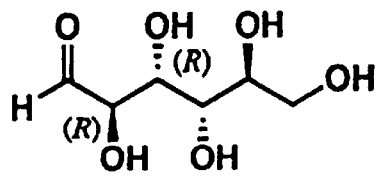
Figure 8B:
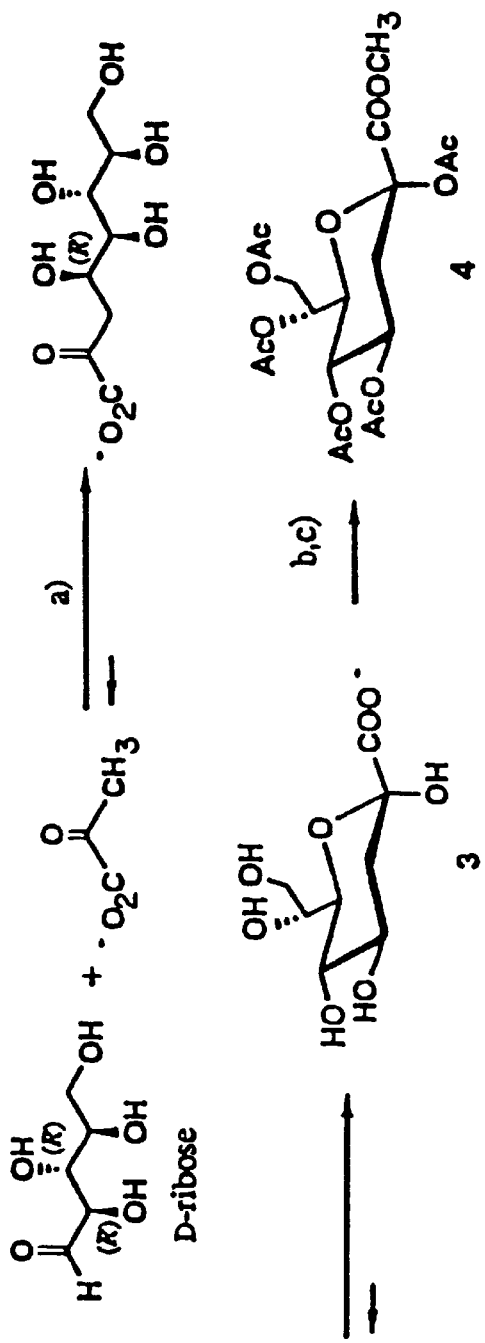
Figure 8C:
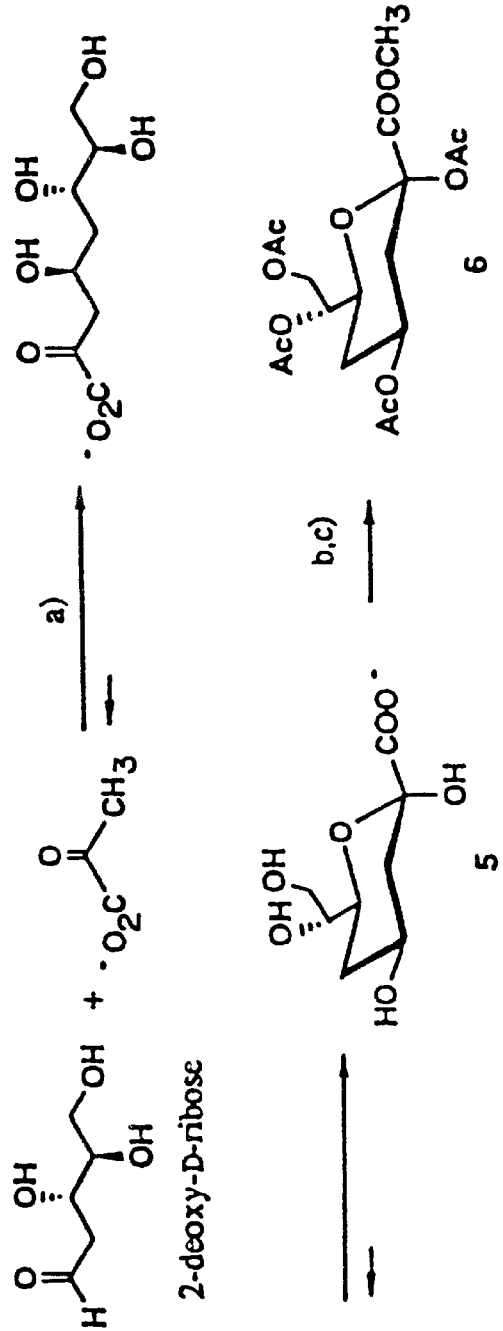

Several substrates with good or fair relative rate are shown to be employable in the aldol condensation. The reactions with D-ribose and 2-deoxy-D-ribose are illustrated in FIGS. 8B and 8C respectively. These reactions took place smoothly to give 3 (57% after derivation to 4) and 5 (47% as 6), respectively. $^1$H NMR spectra of 3, 4, 5, and 6 clearly show a $^5C_2$ pyranose form in both products (Table III). The $^1$H spectrum of 6 is shown in FIG. 2. It is noteworthy that in these cases, even though the relative rates are lower (72% for D-ribose and 71% for 2-deoxy-D-ribose) than that of D-arabinose, TLC analysis of the reaction products showed no starting material left, whereas a substantial amount of starting material always remains in the reaction with D-arabinose. It is suggested that formation of the pyranose form of 3 and 5, where all substituents are located in the stable orientation, further shifted the equilibrium toward condensation.

Figure 8D:
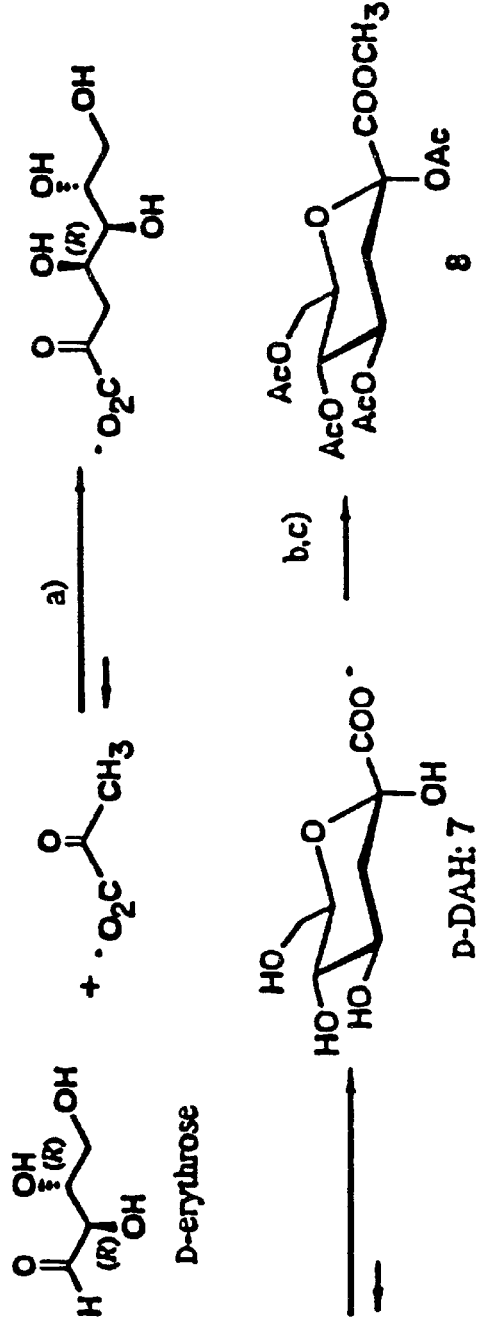
Figure 8E:
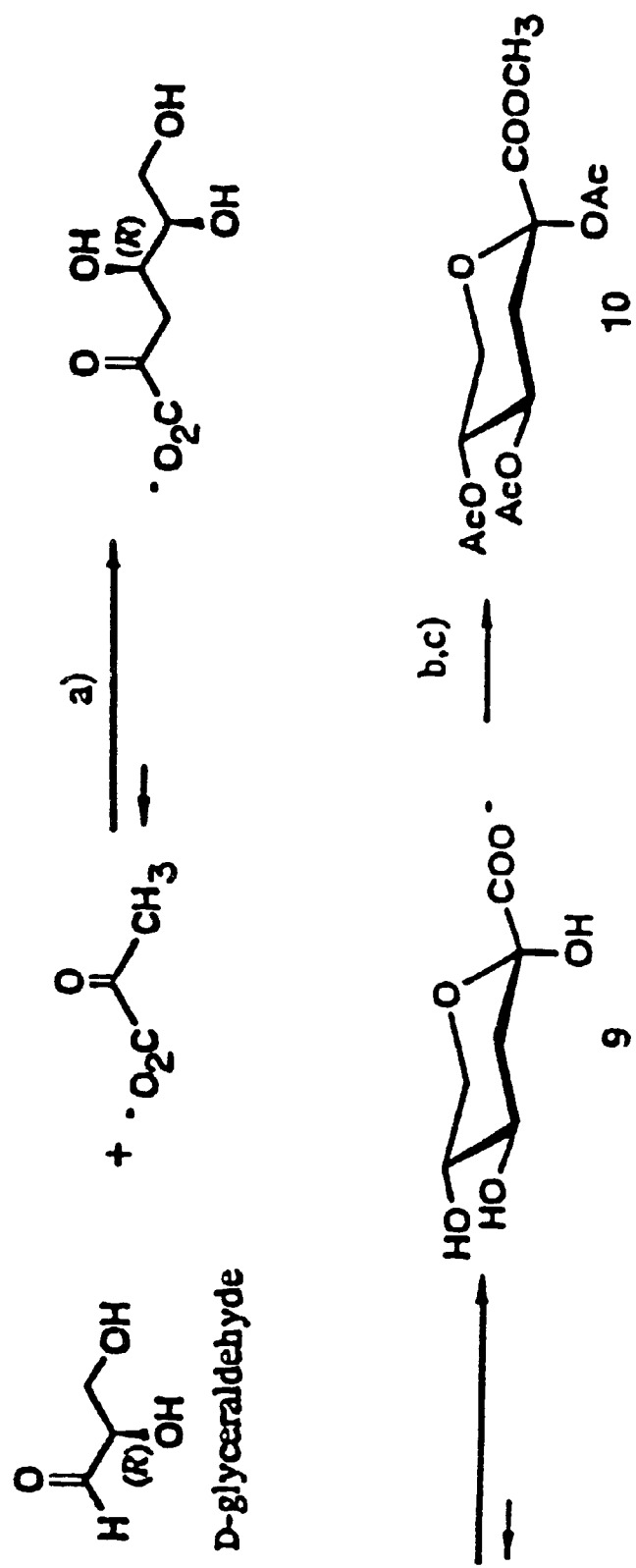

The products 7 (3-deoxy-D-arabino-2-heptulosonic acid, DAH, 39% as 8) and 9 (11% as 10) were also obtained from D-erythrose and D-glyceraldehyde, as illustrated in FIGS. 8D and 8E respectively. These yields indicate that this aldolase-catalyzed condensation is also useful for the synthesis of lower homologs of KDO. The phosphate of 7 (DAHP) plays an important role in the shikimate synthesis pathway in plants and microorganisms. The selected chemical shifts and coupling constants for the $^1$H NMR spectra of products 3–10 are summarized in Table III.

Figure 8F:
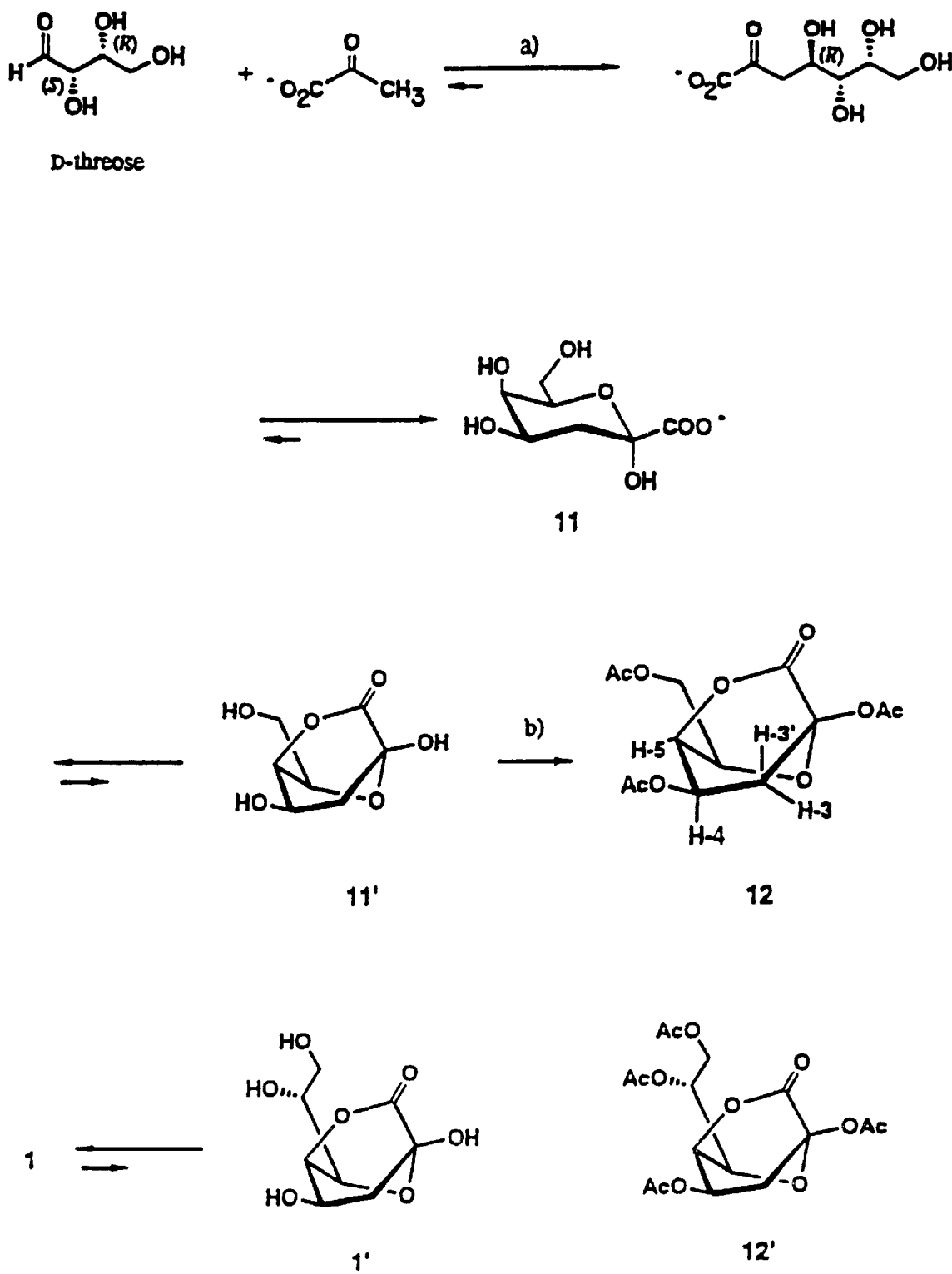
Figure 8G:
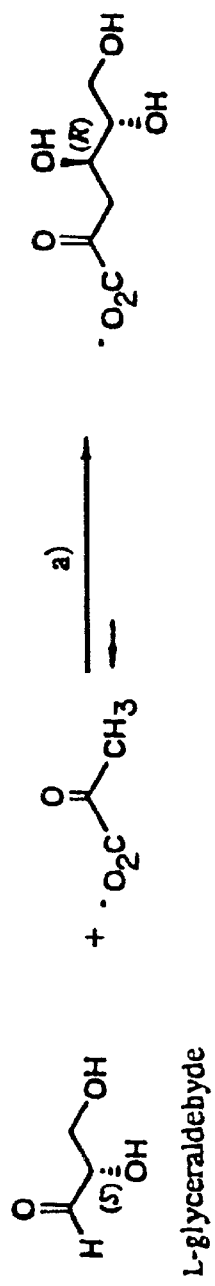
Figure 8G:
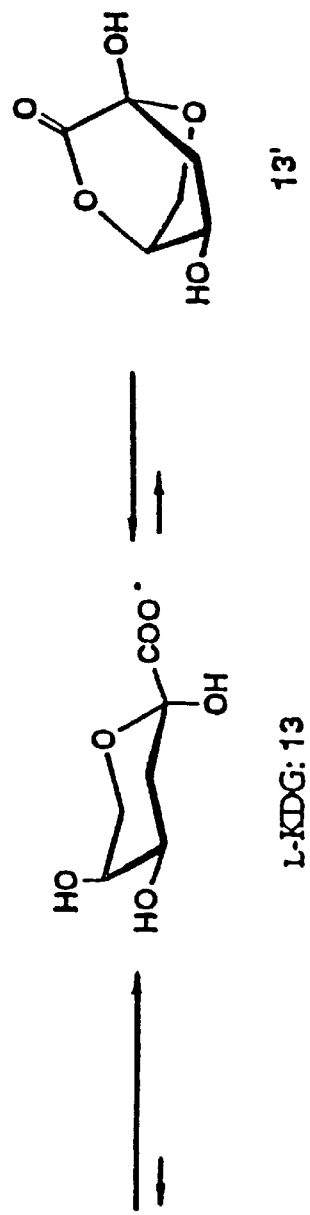
Figure 8G:
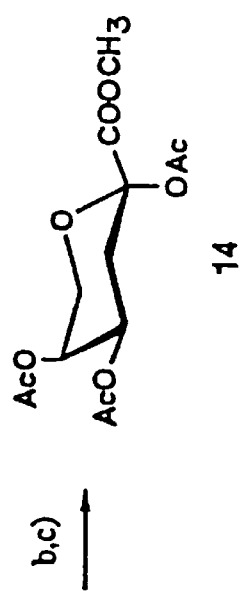

FIG. 8F illustrates the aldolase catalyzed condensation reaction can be employed to produce product 11 from D-threose. Product 11 has a $^1$H NMR spectrum similar to that of KDO. The reaction with L-glyceraldehyde, illustrated in FIG. 8G afforded 13 (2-keto-3-deoxy-L-gluconic acid, KDG), an enantiomer of D-KDG, whose phosphate (KDGP) is an intermediate in the Entner-Doudoroff pathway. (Entner, N.; Doudoroff, M. *J. Biol. Chem.* 1952, 196, 853.) The $^1$H NMR spectrum of 13 was very complicated (see experimental). To clarify the stereochemistry, preparation of derivatives was attempted; however, the products were still difficult to identify. The only isolable component from 11 was a bicyclic lactone. The structure was determined as 12 (FIG. 8F) by comparing its $^1$H NMR spectrum with that of the higher homolog 12', which had been obtained from KDO and unambiguously characterized previously. (Charon, D.; Auzanneau, F.-I.; Mérienne, C.; Szabó, L. *Tetrahedron Lett.* 1987, 23, 1393.)

In its $^1$H NMR spectrum (Table II), a long range coupling between H-3 and H-5 (0.6 Hz) indicates that the pyranose form of the product exists as a twisted boat conformation, and all of the coupling constants are consistent with those observed in the case of 12'. It is interesting that in the spectra of 11, 13 and KDO, a substantial proportion of the similar signals were observed, where one of the H-3 signal appears at very low field (Table II). From these results, it is assumed that the bicyclic 1<<5 lactones 1', 11' and 13' form at nearly neutral pH. The formation of 1<<7 lactone is excluded, since those signals were observed in the case of a hexulosonate 13' without any C-7 hydroxy group. The homologs prepared here also proceed through a spontaneous 1<<5 lactone formation, as already proposed previously for KDO. (Menton, L. D., et al. *Carbohydr. Res.* 1980, 80, 295.) Compound 13 mainly exists as $^5C_2$ pyranose form as indicated in 14.

Figure 8H:
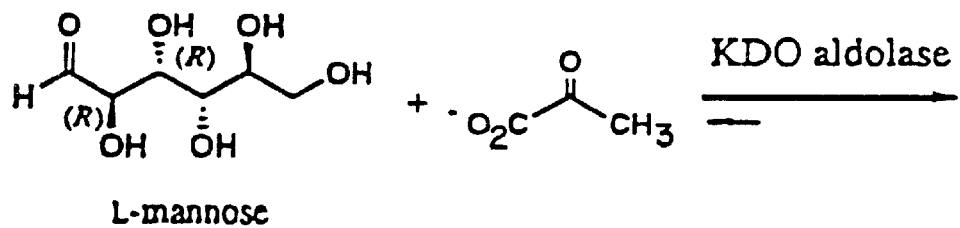
Figure 8H:
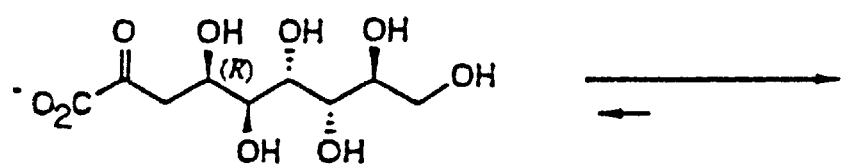
Figure 8H:
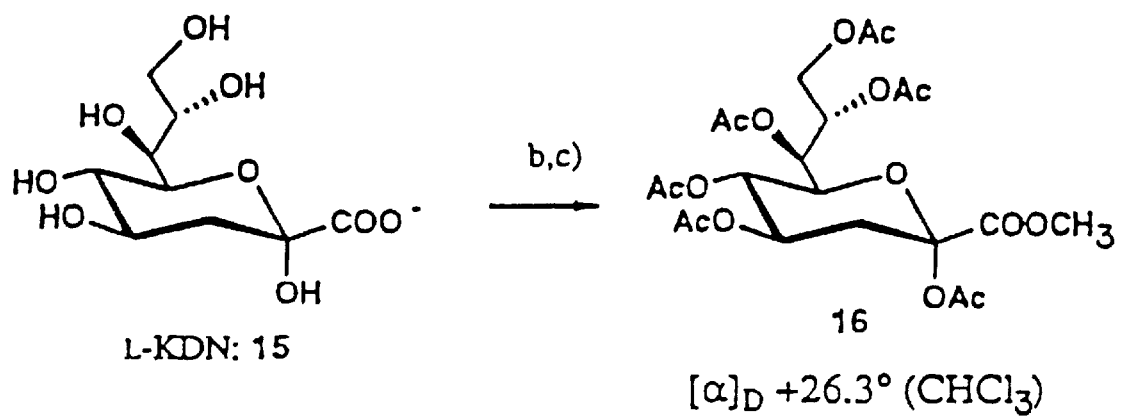
Figure 8I:
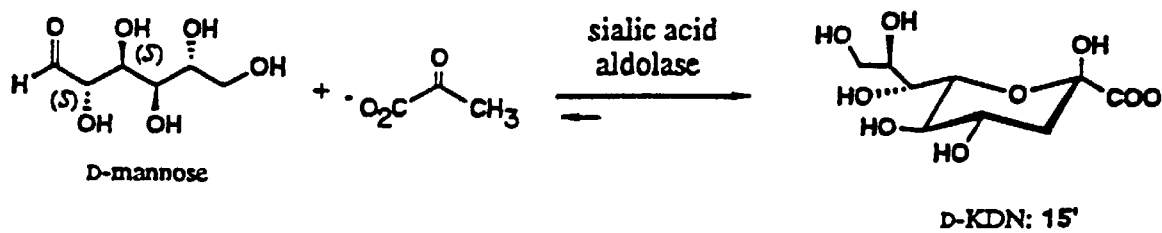
Figure 8I:
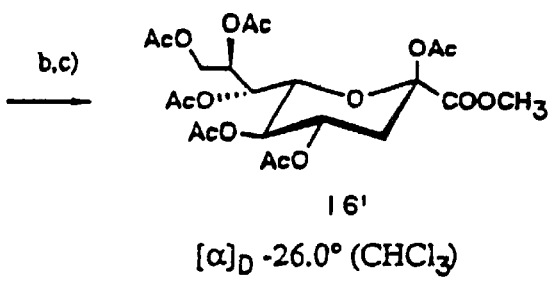
Figure 8I:
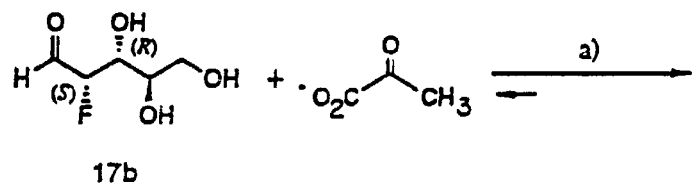
Figure 8I:
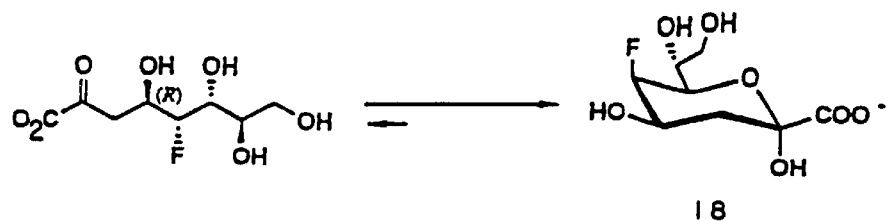
Figure 8I:
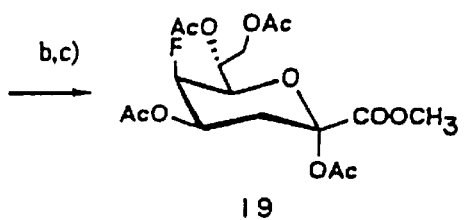

The reaction with L-mannose illustrated in FIG. 8H gave 15 (3-deoxy-L-glycero-L-galacto-2-nonulosonic acid, L-KDN, 61% as 16), which is an enantiomer of D-KDN, a component in polysialoglycoprotein and ganglioside of rainbow trout eggs. (Lin, C.-H., et al., *J. Am. Chem. Soc.*, in press; Nadano, D. et al. *J. Biol. Chem.* 1986, 261, 11550; and Song, Y., et al. *J. Biol. Chem.* 1991, 266, 21929.) The optical rotation [[α]$^{25}$D+26.3° (CHCl$_3$)] and 1H NMR spectrum of 16 were in good accordance with those of 16' [[α]$^{25}$D −26.0° (CHCl$_3$)], which was obtained via reaction with D-mannose catalyzed by sialic acid aldolase, as illustrated in FIG. 8I, except for the sign of rotation (*Tetrahedron* 1990, 46, 201). The availability of both enantiomers of KDN may develop new analogs of sialyl oligosaccharides. (Ichikawa, Y., et al. *Anal. Biochem.* 1992, 202, 215.)

Finally, the aldol reaction with an unnatural sugar containing a fluorine atom was conducted to give 18 (19% of 19). By comparing the $^1$H NMR spectra, the proportion of the β-isomer (10.71) of 18 was ca. 1.5 times higher than that of KDO (6.9%), probably due to the absence of furanose and 1<<5 lactone forms. This result suggests that 18 might be a good substrate for CMP-KDO synthetase, since the enzyme accepts the unstable β-form of KDO as a substrate. (Kohlbrenner, W. E. and Fesik, S. W., *J. Biol. Chem.* 1985, 260, 14695.) We therefore synthesized 18 in a larger scale by combining the use of KDO aldolase and pyruvate decarboxylase, which made the workup procedure much easier. Preliminary study using 18 toward CMP-KDO synthetase which had recently been cloned and over-expressed in this group showed that 18 was accepted to the enzyme.

Figure 3:
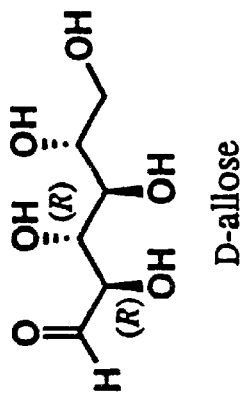
FIG. 3 illustrates saccharides having poor specificity for KDO aldolase isolated from *Aureobacterium barkerei* KDO-37-2.
Figure 3:
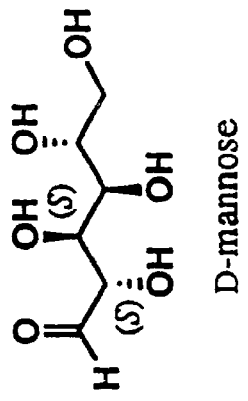
Figure 3:
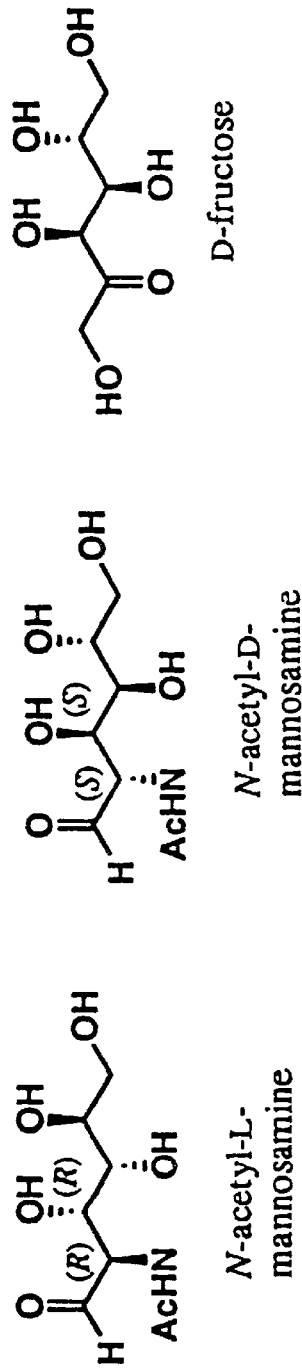
Figure 3:
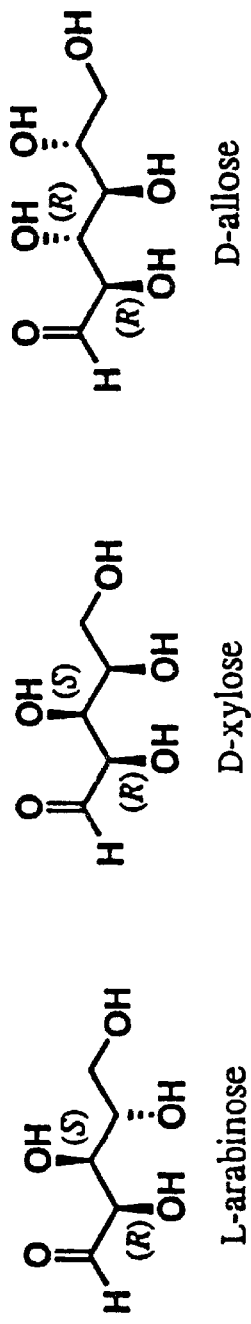
Figure 3:
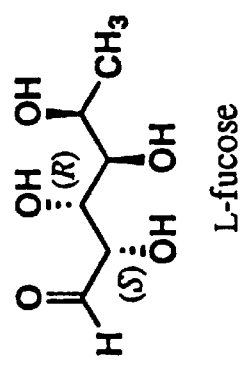
Figure 3:
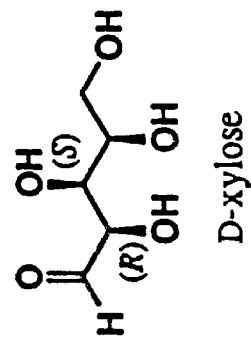
Figure 3:
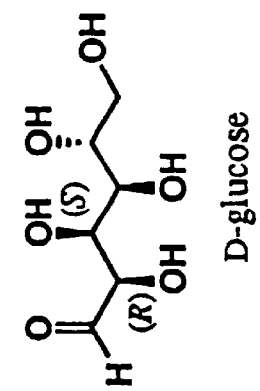
Figure 4:
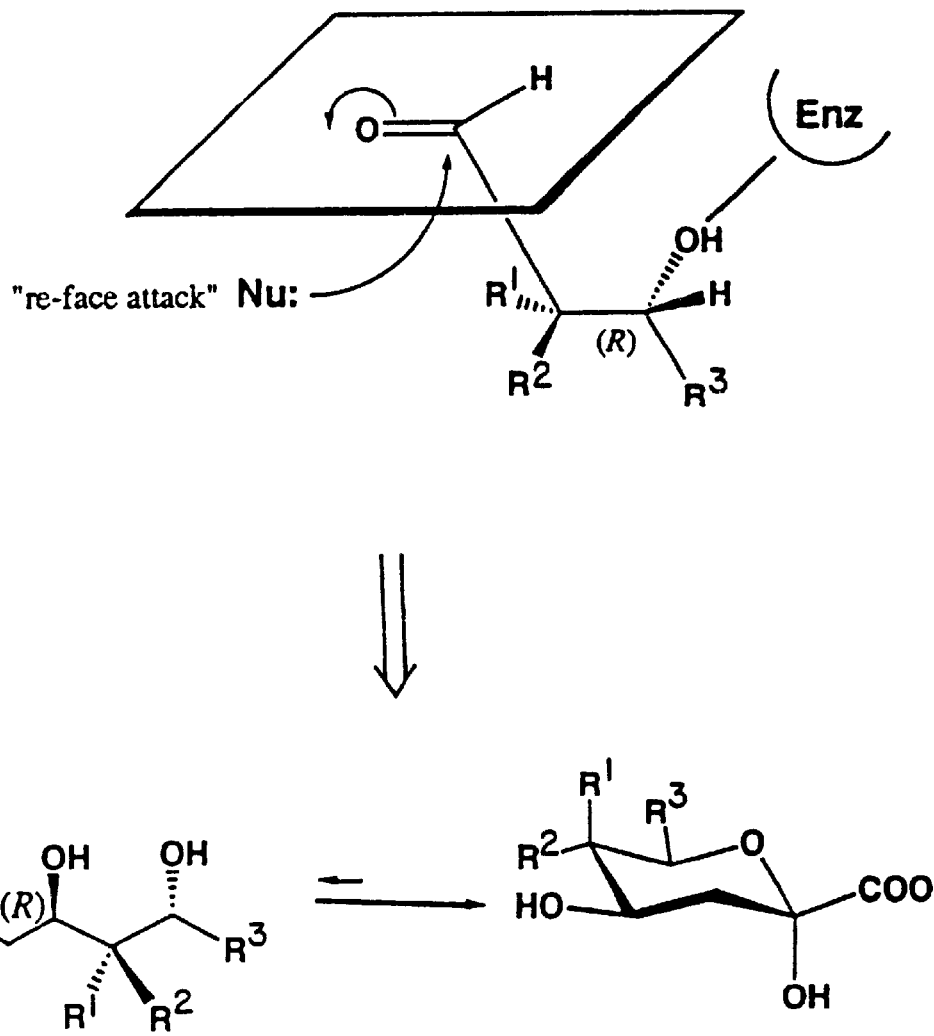
FIG. 4 illustrates the stereochemistry of the aldol condensation catalyzed by KDO aldolase isolated from *Aureobacterium barkerei* KDO-37-2.
Figure 5:
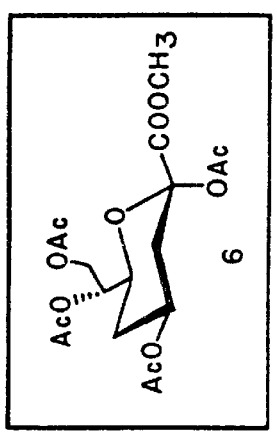
FIG. 5 illustrates the $^1$H NMR spectrum of 6, the product from 2-deoxy-D-ribose (400 MHz), $CDCl_3$.
Figure 5:
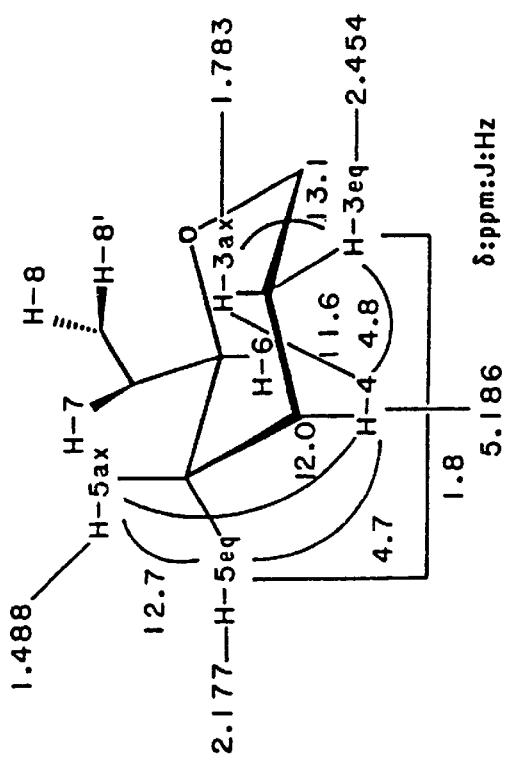
Figure 6:
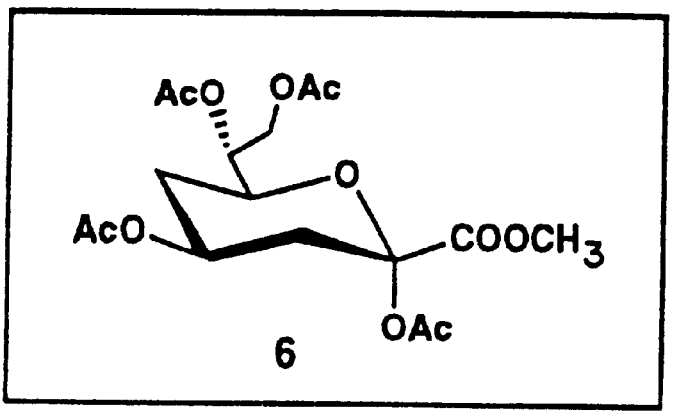
FIG. 6 illustrates the chemical assignment of the $^1$H NMR spectrum compound 6 as shown in FIG. 6.
Figure 6:
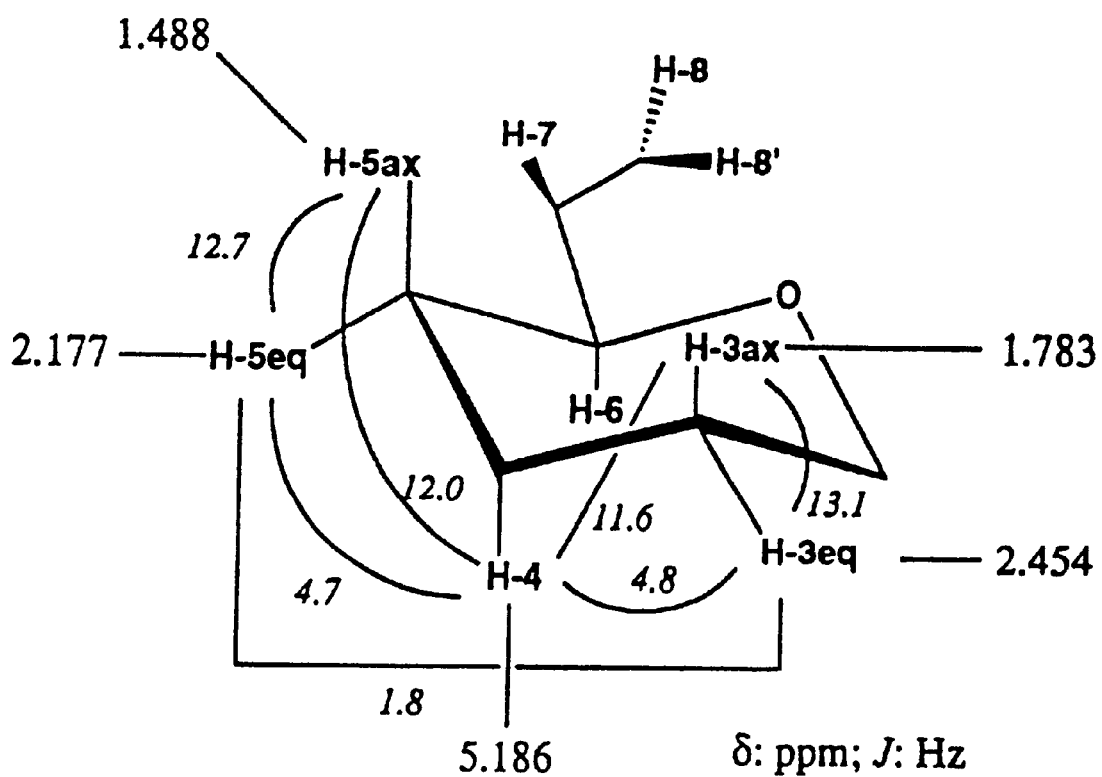

Based on these results, the stereochemical course of the aldol condensation catalyzed by this KDO aldolase is probably as follows: The attack of pyruvate always takes place on the re face of the carbonyl group of the substrates, a facial selection complementary to sialic acid aldolase reactions (si face attack). The stereochemical requirements of substrates and the stereochemical course of the aldol condensation are indicated in FIG. 3. It is concluded that in general the enzyme accepts substrates with an R-configuration at C-3. The substrates with an S configuration at C-2 is kinetically favored, while those with R configuration at C-2 are thermodynamically favored to give a better yield.

Synthesis of Decarboxylated Analogs

Figure 9A:
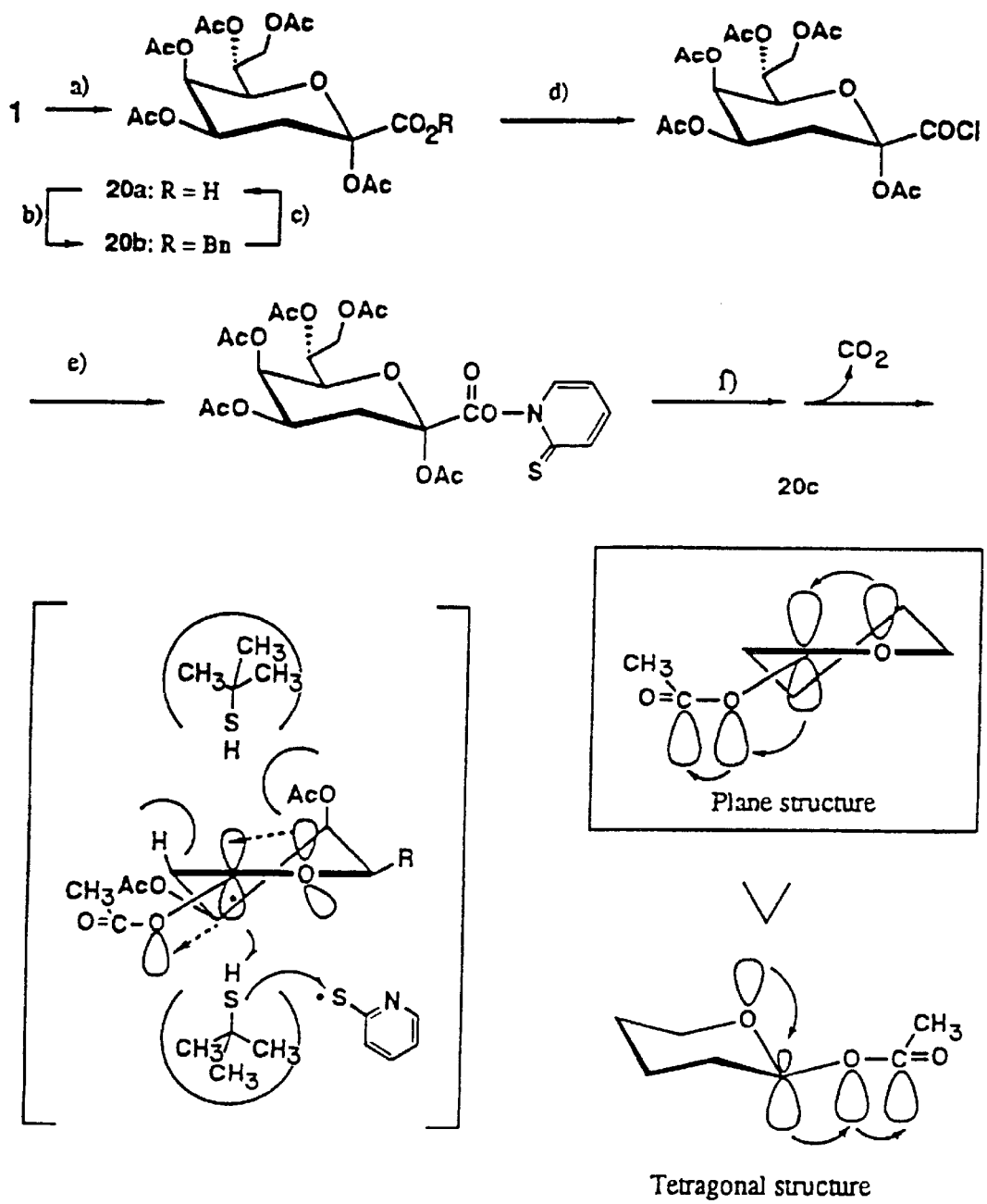
FIGS. 9A and B illustrate a synthetic route employing a decarboxylation of KDO aldolase condensation products.
Figure 9A:
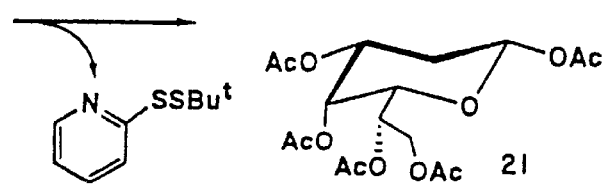
Figure 9B:
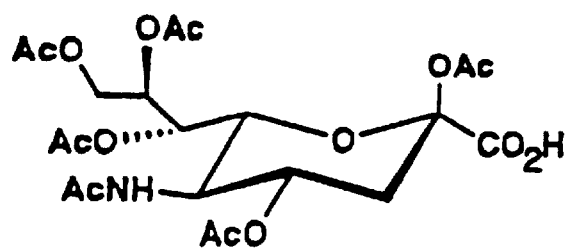
Figure 9B:
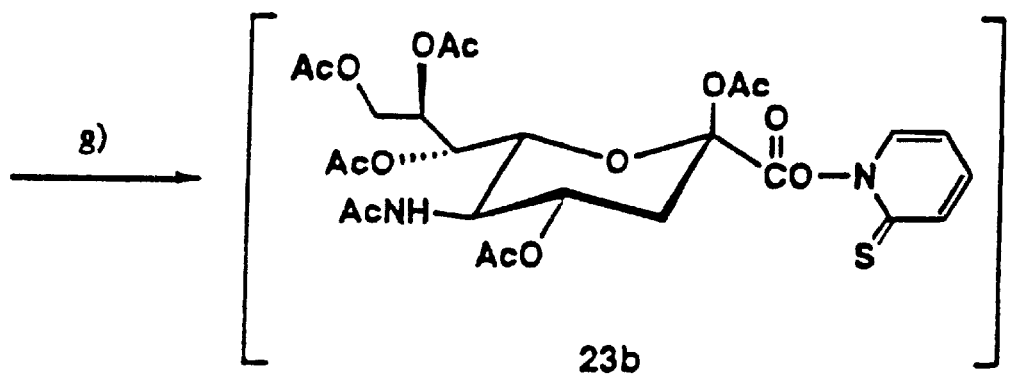
Figure 9B:
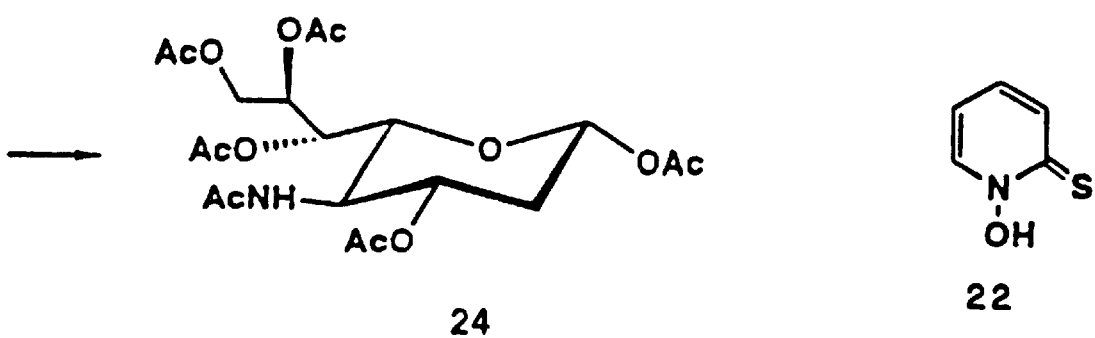

Decarboxylation of KDO and its analogs will yield the corresponding aldose derivatives. A synthetic route employing decarboxylation of KDO aldolase condensation products is illustrated in FIGS. 9A and 9B. The reagents employed in these synthetic routes is as follows:

| Step | Reagent |
| --- | --- |
| (a) | Ac$_2$, DMAP/pyridine |
| (b) | CsCO$_3$, BnBr/DMF |
| (c) | H$_2$, Pd-C/EtOH |
| (d) | (COCl)$_2$/toluene |
| (e) | 22, DMAP/pyridine-toluene |
| (f) | t-BuSH, hν |
| (g) | Et$_2$NCH$_2$CH$_2$CH$_2$N=C=NEt.HCl (WSCI)-Cl, 22 (5 eq.), t-BuSH, DMAP, Et$_3$N, MS 4Å/CH$_2$Cl$_2$, hν |

The aldodeoxyheptose structure is particularly interesting since a number of heptoses are widely distributed in nature, some of which play important roles in metabolic pathways. Barton's radical-mediated decarboxylation of the penta-O-acetyl derivative 20a obtained from the corresponding benzyl ester 20b seems to be the most straightforward route to the desired heptose derivative 21. (e.g., Crich, D. and Lim, L. B. L. *J. Chem. Soc. Perkin I* 1991, 2209 and Auzanneau, F.-I. et al. *Carbohydr. Res.* 1990, 201, 337.)

There have recently been growing interests in the synthesis of physiologically active carbohydrate- and nucleic acid-related compounds via anomeric radical intermediates. It appears to us that radical-mediated reaction stabilized both electron withdrawing and donating group (capto-dative effect), e.g. Viehe, H. G. et al. *Acc. Chem. Res.* 1985, 18, 148.) at anomeric position [—C(●)(OAc)O-type] is rare (only a few related examples [eg. —C(●)(CO$_2$Me)O-type, —C(●)(CHF$_2$)O-type] are known), while examples in the case of simple anomeric radical [—C(●)(H or R)O-type] and the one bearing two electron donating oxygen atom [—C(●)(OR))-type] have been extensively studied. (e.g. Crich, D. and Lim, L. B. L. *J. Chem. Soc. Perkin I* 1991, 2205 and *J. Chem. Soc. Perkin I* 1991, 2209; Schmidt, R. et al. *Tetrahedron Lett.* 1988, 29, 3643; Myrvold, S. et al. *J. Am. Chem. Soc.* 1989, 111, 1861; Motherwell, W. B. et al. *Synlett.* 1989, 68; and Samadi, M. *J. Med. Chem.* 1992, 35, 63.) The radical intermediate was formed by the thermal decomposition of the thiohydroxamate 20c generated in situ from the corresponding acid chloride and 22 in the presence of azobisisobutyronitrile (AIBN). The subsequent trapping with tributyltin hydride resulted in only a disappointing (less than 2%) yield of 21. The yield was, however, dramatically improved to 68% by irradiation with white light in the presence of t-butylmercaptane.

The $^1$H NMR spectrum of 21 clearly shows the exclusive β-anomer (δ5.75, dd, J$_{1,2eq}$=3.0, J$_{1,2ax}$=10.0 Hz, H-1), indicating that the abstraction of hydrogen atom from t-butylmercaptane took place at the bottom side of the six-membered ring. The proposed mechanism for the exclusive formation of β-isomer is as follows. The stable conformer of the radical intermediate which is stabilized both by the electron-donating and withdrawing effects is supposed to be in a plane form as depicted in FIGS. 9A and 9B, which allows the maximum interaction between the one-electron p orbital and the lone pair electrons on the adjacent ring oxygen. t-Butylmercaptane is easily accessible from the bottom side, while the approach from the top side is sterically hindered by the hydrogen and acetoxy groups. This explanation in terms of kinetic control is well matched with the thermodynamic stability of the β-product.

The radical process was also applied to the synthesis of the decarboxylated analog of N-acetylneuraminic acid. It turned out, however, that all attempts for the synthesis of the acyl chloride resulted in a complex mixture, even from fully protected peracetate form 23a of sialic acid, because NHAc proton still has a substantial reactivity to chlorinating reagents. The direct formation of thiohydroxamate 23b was also found to be difficult because of the inherent steric hindrance around carbonyl group in the starting material. Through an extensive examination of the reaction conditions, it was found that the combination of ethyl (diethylamino)pronylcarbodiimide hydrochloride (WSCI-Cl, 1.5 eq) and excess of 22 (5.0 eq) worked well for the in situ formation and degradation of thiohydroxamate, to give 24 (27% yield from 23a). This condition has the advantage that the reaction can be carried out in one step. The newly formed product was exclusively an α-anomer where the OAc group is located in the equatorial orientation, consistent with the result obtained in the decarboxylation of KDO derivative. (Haverkamp, J. et al. *Eur. J. Biochem.* 1982, 122, 305.)

PREPARATION OF EXAMPLES

General

Optical rotations were measured on Perkin-Elmer 241 spectrophotometer UV and visible spectra were recorded on a Beckmann DU-70 spectrometer. $^1$H and $^{13}$C NMR spectra were recorded at 400 and 500 MHz on Bruker AMX-400 and AMX-500 spectrometer. High-resolution mass spectra (HRMS) were recorded on a VG ZAB-ZSE mass spectrometer under fast atom bombardment (FAB) conditions. Column chromatography was carried out with silica gel of 70–230 mesh. Preparative TLC was carried out on Merck Art. 5744 (0.5 mm).

Isolation of the Microorganism

*Aureobacteriur barkerei* containing high levels of KDO aldolases was selected with the S medium containing 0.25% of synthetic KDO mixture as carbon source (20 mL) in serum bottles (158 mL) and incubated at 37° C. for 2 days with shaking (250 r.p.m.). (McNicholas, P. A. et al. *Carbohydr. Res.* 1986, 146, 219 and Shirai, R.; and Ogura, H. *Tetrahedron Lett.* 1989, 30, 2263.) The bottles which showed turbidity were transferred to the same fresh medium. After several transfers, the cultures were plated on the S medium agar plates (1.5% agar) containing 0.25% of synthetic KDO mixture. The isolated colonies were transferred to the liquid medium as described above. To confirm the utilization of KDO, the disappearance in the medium was monitored by TLC as described in the synthesis of KDO. The cultures which showed the utilization of KDO were harvested by centrifugation and resuspended in 50 mM phosphate buffer (pH 7.0). The cell suspension was incubated with 1% (w/v) of authentic KDO (from Sigma) at 37° C. overnight to confirm the degradation of KDO by TLC. The cultures were then replated on LB agar plates to ensure the purity of the culture.

Preparation of the Enzyme

With one slight modification, the incubation was carried out according to the procedure reported by Gharambor (supra). The ingredients of the medium were as follows: $NH_4Cl$ (5 g), $K_2SO_4$ (1 g), $MgSO_4 \cdot 7H_2O$ (200 mg), $CaCl_2$ (20 mg), $FeSO_4 \cdot 7H_2O$ (1 mg), yeast extract (1 g), $Na_2HPO_4 \cdot 7H_2O$ (10 g), and $KH_2PO_4$ (3 g) in distilled water (1 L), at pH 7.2. To a 50 mL of this medium in a 100 mL Erlenmeyer flask, were added D-glucose (40% solution in water, 25 µL) and KDO (100 mg, 0.2%), and a loopful of *Aureobacterium barkerei* KDO-37-2 was incolutated. The flask was shaken at 250 r.p.m. on a gyrorotary shaker at 30° C. for 16 h. The seed culture thus obtained was poured into the 1950 mL of the same incubation medium containing KDO (3.9 g). The mixture was divided and poured into two of 2.8 L Erlenmeyer flasks. The flasks were shaken at 250 r.p.m. at 30° C. for 24 h. The growth of microorganism was estimated by OD at 600 nm to be 1.90. The cells were harvested at 10,000×g for 30 min at 4° C. and washed with 50 mM potassium-sodium phosphate buffer (pH 7.5). The collected cells were then resuspended in the same buffer solution (20 mL) and disrupted by French-pressure apparatus (at 16,000 lb/in). The cell debris were removed by centrifuge at 23,000×g for 1 h at 4° C. to give the supernatant (ca. 20 mL) as the crude enzyme preparation. The enzyme activity was determined to be 1.45 U/mL for the degradation of KDO according to the method of Aminoff (*Biochem. J.* 1961, 81, 384). Ammonium sulfate precipitation between 45–75% saturation was collected and dialyzed in phosphate buffer (2 L; 100 mM, 1 mM of dithiothreitol, 2 L) to give partially purified enzyme (13.5 mL, 1.73 U/mL for KDO degradation), according to the method of Kim (*J. Am. Chem. Soc.* 1988, 110, 6481)

Kinetic Measurements

The rates for aldolase-catalyzed reactions were obtained by measuring the amount of remaining pyruvate, according the method of Kim (supra). The reactions were carried out in 0.1 M phosphate buffer (pH 7.5) containing: varied concentrations of pyruvate, 2.0, 3.33, 5, and 10 mM; varied concentrations of D-arabinose, 0.2, 0.25, 0.33, and 0.50 M in 0.5 mL of solution. Each solution was incubated at 37° C. Periodically, a small aliquot (25–100 µL) was withdrawn and mixed with an assay solution (1.4 mL) containing 0.1 M phosphate (pH 7.5) buffer, 0.3 mM NADH, and 20–30 U of L-lactate dehydrogenase. The decrease in absorbance at 340 nm was measured and converted into the amount of the unreacted pyruvate using 6220 $M^{-1}cm^{-1}$ for the molecular absorbance of NADH. The kinetic parameters were obtained from the Lineweaver-Burk plots.

For the relative rate measurements, the concentration of pyruvate (fluoropyruvate) and sugar were fixed at 10 mM and 0.5 M, respectively. Other conditions were the same as above.

Example 1

Ammonium 3-deoxy-α-D-manno-2-octulosonate monohydrate (KDO azmonium salt monohydrate, 1)

D-Arabinose (250 mg, 1.67 mmol), sodium pyruvate (1.83 g, 16.7 mmol), dithiothreitol (1.5 mg), $NaN_3$ (2% solution in water, 100 µL), $NaHPO_4 \cdot 7H_2O$ (53 mg), and $KH_2PO_4$ (13 mg) were added to the KDO aldolase (5.1 U, 10 mL). The pH was adjusted to 7.5 and the mixture was stirred under $N_2$ at 30° C. for 3 days. The product was purified by treatment with a Dowex-1 resin column (bicarbonate form) eluted with a linear gradient from 0 to 0.25 M of ammonium bicarbonate. KDO ammonium salt was further purified by Biogel P-2 column. The fraction eluted with $H_2O$ containing KDO was collected and its total amount was estimated to be 1.11 mmol (67%) by Aminoff's assay (supra). The residue after lyophilization was recrystallized from aqueous ethanol to give colorless plates (168 mg, 37% from D-arabinose): mp 123–125° C. (decomposition) [lit. according to Hershberger: mp 121–123° C., authentic sample from Sigma mp 123–125° C. (decomposition)]; $[\alpha]^{26}D$ +40.3° (c 2.06, water) [lit. according to Hershberger: $[\alpha]^{27}D$ +42.3° (c 1.7, water), authentic sample from Sigma $[\alpha]^{26}D$ +40.2° (c 2.03, water)]. Its $^1H$ NMR spectrum in $D_2O$ was identical with that of an authentic sample. (Hershberger: *J. Biol. Chem.* 1968, 243, 1585.) A small portion was converted to pentaacetate methyl ester derivative 2: $^1H$ NMR ($CDCl_3$) δ1.994 (3H, s, acetyl), 1.998 (3H, s, acetyl), 2.045 (3H, s acetyl), 2.108 (3H, s, acetyl), 2.139 (3H, s, acetyl), 2.201 (1H, dd, $J_{3ax,4}$=12.0, $J_{3ax,3eq}$=13.0 Hz, H-3ax), 2.245 (1H, dd, $J_{3eq,4}$=6.0, $J_{3eq,3ax}$=13.0 Hz, H-3eq), 3.810 (3H, s, $COOCH_3$), 4.113 (1H, dd, $J_{8',7}$ =12.5, $J_{8',8}$ =12.5 Hz, H-8'), 4.173 (1H, dd, $J_{6,5}$=1.3, $J_{6,7}$=9.5 Hz, H-6), 4.475 (1H, dd, $J_{8,7}$=4.0, $J_{8,8'}$=12.5 Hz, H-8), 5.220 (1H, ddd, $J_{7,8}$=4.0, $J_{7,6}$=9.5, $J_{7,8'}$=12.5 Hz, H-7), 5.322 (1H, ddd, $J_{4,5}$=3.0, $J_{4,3eq}$=6.0, $J_{4,3eq}$=6.0, $J_{4,3ax}$=12.0 Hz, H-4), 5.385 (1H, dd, $J_{5,6}$=1.3, $J_{5,4}$=3.0 Hz, H-5). The $^1H$ NMR spectrum was in good accordance with that reported previously by Unger (*Adv. Carbohydr. Chem. Biochem.* 1981, 38, 323).

Example 2

Methyl 2,4,5,7,8-penta-O-acetyl-3-deoxy-α-D-altro-2-octulosonate (4)

In the same manner as described for the preparation of 1, the product 3 (as ammonium salt) was prepared from D-ribose (0.33 mmol): $^1H$ NMR ($D_2O$) δ1.773 (1H, dd, $J_{3ax,4}$=11.9, $J_{3ax,3eq}$=13.0 Hz, H-3ax), 2.148 (1H, dd, $J_{3eq,4}$=5.1, $J_{3eq,3ax}$=13.0 Hz, H-3eq), 3.500 (1H, dd, $J_{5,4}$=9.1, $J_{5,6}$=10.0 Hz, H-5), 3.745 (1H, dd, $J_{8,7}$=7.3, $J_{8,8'}$=12.1 Hz, H-8), 3.789 (1H, dd, $J_{8',7}$=3.7, $J_{8',8}$=12.1 Hz, H-8'), 3.809

(1H, dd, $J_{6,7}$=2.8, $J_{6,5}$=10.0 Hz, H-6), 3.901 (1H, ddd, $J_{4,3eq}$=5.1, $J_{4,5}$=9.1, $J_{4,3ax}$=11.9 Ha, H-4), 4.004 (1H, dd, $J_{7,6}$=2.8, $J_{7,8'}$=3.7, $J_{7,8}$=7.3 Hz, H-7). This was converted to 4 by the successive treatment with acetic anhydride-pyridine-DMAP (see also the preparation of 20b) and etherial diazomethane solution. The product was purified with silica gel preparative TLC to afford 4 (87.7 mg, 57% from D-ribose) as an oil, $[\alpha]^{25}$D +70.9° (c 0.81, CHCl$_3$); $^1$H NMR (CDCl$_3$) δ2.010 (1H, dd, $J_{3ax,4}$=11.6, $J_{3ax,3eq}$=13.5 Hz, H-3ax), 2.030 (3H, s, acetyl), 2.050 (3H, s, acetyl), 2.064 (3H, s, acetyl), 2.105 (3H, s, acetyl), 2.154 (3H, s, acetyl), 2.559 (1H, dd, $J_{3eq,4}$=5.2, $J_{3eq,3ax}$=13.5 Hz, H-3eq), 3.793 (3H, s, COOCH$_3$), 4.084 (1H, dd, $J_{6,7}$=3.2, $J_{6,5}$=10.3 Hz, H-6), 4.241 (1H, dd, $J_{8,7}$=7.0, $J_{8,8'}$=12.0 Hz, H-8), 4.415 (1H, dd, $J_{8',7}$=4.0 $J_{8',8}$=12.0 Hz, H-8'), 5.110 (1H, dd, $J_{5,4}$=9.3, $J_{5,6}$=10.3 Hz, H-5), 5.169 (1H, ddd, $J_{7,6}$=3.2, $J_{7,8'}$=4.0, $J_{7,8}$=7.0 Hz, H-7), 5.271 (1H, ddd, $J_{4,3eq}$=5.2, $J_{4,5}$=9.3, $J_{4,3ax}$=11.6 Hz, H-4); $^{13}$C NMR (CDCl$_3$) δ20.52, 20.56, 20.56, 20.67, 20.67, 35.47, 53.12, 61.23, 68.33, 68.96, 69.85, 71.98, 96.66, 166.21, 167.94, 169.52, 169.85, 169.89, 170.38. HRMS (M+Cs$^+$) calcd C$_{19}$H$_{26}$O$_{13}$Cs 595.0428, found 595.0428.

Example 3

Methyl 2,4,7,8-tetra-O-acetyl-3,5-dideoxy-α-D-manno-2-octulosonate (6)

In the same manner as 3, the product 5 (as ammonium salt) was prepared from 2-deoxy-D-ribose (0.33 mmol): $^1$H NMR (D$_2$O) δ1.400 (1H, ddd, $J_{5ax,4}$=11.9, $J_{5ax,6}$=11.9, $J_{5ax,5eq}$=12.3 Hz, H-5ax), 1.591 (1H, dd, $J_{3ax,4}$=12.1, $J_{3ax,3eq}$=12.7 Hz, H-3ax), 2.009 (1H, dddd, $J_{5eq,3eq}$=1.8, $J_{5eq,6}$=2.2, $J_{5eq,4}$=4.6, $J_{5eq,5ax}$=12.3 Hz, H-5eq) 2.094 (1H, dd, $J_{3eq,5eq}$=1.8, $J_{3eq,4}$=4.6, $J_{3eq,3ax}$=12.7 Hz, H-3eq), 3.398 (1H, dd, $J_{8,7}$=7.1, $J_{8,8'}$=11.8 Hz, H-8), 3.588 (1H, dd, $J_{8',7}$=4.1, $J_{8',8}$=11.8 Hz, H-8'), 3.786 (1H, ddd, $J_{7,8'}$=4.1, $J_{7,6}$=4.6, $J_{7,8}$=7.1 H8, H-7), 3.945 (1H, ddd, $J_{6,5eq}$=2.2, $J_{6,7}$=4.6, $J_{6,5ax}$=11.9 Hz, H-6), 4.112 (1H, dddd, $J_{4,3eq}$=4.6, $J_{4,5eq}$=4.6, $J_{4,5ax}$=11.9, $J_{4,3ax}$=12.1 Hz, H-4). This was converted to 6 (62.2 mg, 47% from 2-deoxy-D-ribose): $[\alpha]^{25}$D +86.0° (c 0.56, CHCl$_3$); $^1$H NMR (CDCl$_3$) δ1.488 (1H, ddd, $J_{5ax,4}$=12.0, $J_{5ax,6}$=12.0, $J_{5ax,5eq}$=12.7 Hz, H-5ax), 1.783 (1H, dd, $J_{3ax,4}$=11.6, $J_{3ax,3eq}$=13.1 Hz, H-3ax), 2.045 (3H, s, acetyl), 2.054 (3H, s, acetyl), 2.070 (3H, s, acetyl), 2.123 (3H, s, acetyl), 2.177 (1H, dddd, $J_{5eq,3eq}$=1.8, $J_{5eq,6}$=2.2, $J_{5eq,4}$=4.7, $J_{5eq,5ax}$=12.7 Hz, H-5eq), 2.454 (1H, dd, $J_{3eq,5eq}$=1.8, $J_{3eq,4}$=4.8, $J_{3eq,3ax}$=13.1 Hz, H-3eq), 3.782 (3H, s, COOCH$_3$), 4.034 (1H, ddd, $J_{6,5eq}$=2.2, $J_{6,7}$=7.6, $J_{6,5ax}$=12.0 Hz, H-6), 4.169 (1H, dd $J_{8,7}$=5.1, $J_{8,8'}$=12.2 Hz, H-8), 4.457 (1H, dd, $J_{8',7}$=2.8, $J_{8',8}$=12.2 Hz, H-8'), 5.093 (1H, ddd, $J_{7,8'}$=2.8, $J_{7,8}$=5.1, $J_{7,6}$=7.6 Hz, H-7), 5.186 (1H, dddd, $J_{4,5eq}$=4.7, $J_{4,3eq}$=4.8, $J_{4,3ax}$=11.6, $J_{4,5ax}$=12.0 Hz, H-4); $^{13}$C NMR (CDCl$_3$) δ20.56, 20.56, 20.73, 20.96, 32.21, 36.03, 52.96, 61.82, 65.72, 69.00, 71.96, 97.61, 167.02, 167.96, 169.81, 170.06, 170.32. HRMS (M+Cs$^+$) calcd C$_{17}$H$_{24}$O$_{11}$Cs 537.0373, found 537.0373.

Example 4

Methyl 2,4,5,7-tetra-O-acetyl-3-deoxy-α-D-arabino-2-heptulosonate (8)

7: $^1$H NMR (D$_2$O) δ1.773 (1H, dd, $J_{3ax,4}$=11.8, $J_{3ax,3eq}$=13.0 Hz, H-3ax), 2.180 (1H, dd, $J_{3eq,4}$=5.1, $J_{3eq,3ax}$=13.0 Hz, H-3eq), 3.433 (1H, dd, $J_{5,4}$=9.2, $J_{5,6}$=9.5 Hz, H-5), 3.744 (1H, ddd, $J_{6,7}$=3.5, $J_{6,7'}$=3.5, $J_{6,5}$=9.5 Hz, H-6) 3.807 (1H, m, H-7), 3.812 (1H, m, H-7'), 3.930 (1H, ddd, $J_{4,3eq}$=5.1, $J_{4,5}$=9.2, $J_{4,3a}$=11.8 Hz, H-4).

8: (50.0 mg, 39% from 0.33 mmol of D-erythrose): $[\alpha]^{25}$D +54.0° (c 0.50, CHCl$_3$); $^1$H NMR (CDCl$_3$) δ2.034 (3H, s, acetyl), 2.053 (3H, s, acetyl), 2.087 (3H, s, acetyl), 2.087 (1H, dd, $J_{3ax,4}$=11.4, $J_{3ax,3eq}$=13.6 Hz, H-3ax), 2.173 (3H, s, acetyl), 2.658 (1H, dd, $J_{3eq,4}$=5.2, $J_{3eq,3ax}$=13.6 Hz, H-3eq) 3.808 (3H, s, COOCH$_3$) 4.058 (1H, dd, $J_{6,7}$=2.3, $J_{6,7'}$=4.3, $J_{6,5}$=10.2 Hz, H-6), 4.100 (1H, $J_{7,6}$=2.3, $J_{7,7'}$=12.4 Hz, H-7), 4.355 (1H, $J_{7',6}$=4.3, $J_{7',7}$=12.4 Hz; H-7'); $^{13}$C NMR (CDCl$_3$) δ20.65, 20.76, 20.76, 20.84, 35.58, 53.31, 61.69, 68.16, 68.37, 71.51, 97.29, 166.41, 168.43, 169.61, 170.13, 170.77. HRMS (M+Cs$^+$) calcd C$_{16}$H$_{22}$O$_{11}$Cs 523.0216, found 523.0216.

Example 5

Methyl 2,4,5-tri-O-acetyl-2-keto-3-deoxy-α-D-galactonate (10)

9: $^1$H NMR (D$_2$O) δ1.795 (1H, dd, $J_{3ax,4}$=11.6, $J_{3ax,3eq}$=13.1 Hz, H-3ax), 2.176 (1H, dd, $J_{3eq,4}$=5.1, $J_{3eq,3ax}$=13.1 Hz, H-3eq), 3.60–3.65 (2H, m), 3.77–3.91 (2H, m).

10: (11.0 mg, 11% from 0.33 mmol of D-glyceraldehyde): $[\alpha]^{25}$D +31.8° (c 1.10, CHCl$_3$); $^1$H NMR (CDCl$_3$) δ1.948 (1H, dd, $J_{3ax,4}$=11.2, $J_{3ax,3eq}$=13.5 Hz, H-3ax), 2.055 (3H, s, acetyl), 2.059 (3H, s, acetyl), 2.170 (3H, s, acetyl), 2.618 (1H, dd, $J_{3eq,4}$=5.2, $J_{3eq,3ax}$=13.5 Hz, H-3eq), 3.629 (1H, dd, $J_{6ax,5}$=10.6, $J_{6ax,6eq}$=11.3 Hz, H-6ax), 3.809 (3H, s, COOCH$_3$), 4.149 (1H, dd, $J_{6eq,5}$=5.7, $J_{6eq,6ax}$=11.3 Hz, H-6eq), 5.049 (1H, ddd, $J_{5,6eq}$=5.7, $J_{5,4}$=9.5, $J_{5,6ax}$=10.6 Hz, H-5), 5.320 (1H, ddd, $J_{4,3eq}$=5.2, $J_{4,5}$=9.5, $J_{4,3ax}$=11.2 Hz, H-4); $^{13}$C NMR (CDCl$_3$) δ20.67, 20.72, 20.89, 35.81, 53.25, 62.17, 67.66, 68.49, 96.80, 166.96, 168.50, 169.84, 170.05. HRMS (M+Cs$^+$) calcd C$_{13}$H$_{18}$O$_9$Cs 451.0005, found 451.0005.

Example 6

2,4,7-Tri-O-acetyl-3-deoxy-α-D-lyxo-2-heptulosonic acid 1<<5 lactone (12)

11: $^1$H NMR (D$_2$O) δ1.90–1.98 (m, H-3 of the major component); a minor pair of H-3 protons: 2.072 (dd, $J_{3,4}$=3.1, $J_{3,3'}$=14.2 Hz, H-3), 2.576 (dd, $J_{3',4}$=7.3, $J_{3',3}$=14.2 Hz, H-3'); another minor pair of H-3 protons: 2.301 (dd, J=7.0, 13.4 Hz), 2.384 (dd, J=7.0, 13.4 Hz); 3.60–3.95 (m), 3.95–4.20 (m), 4.48–4.52 (m).

12: (1.9 mg): $^1$H NMR (CDCl$_3$) δ2.096 (3H, s, acetyl), 2.127 (3H, s, acetyl), 2.180 (3H, s, acetyl), 2.339 (1H, ddd, $J_{3,5}$=0.6, $J_{3,4}$=2.4, $J_{3,3'}$=14.9 Hz, H-3), 2.972 (1H, dd, $J_{3',4}$=9.4, $J_{3',3}$=14.9 Hz, H-3'), 4.180 (1H, ABX type, $J_{6,7}$=5.6, $J_{6,7'}$=9.9 Hz, H-6), 4.28–4.35 (2H, m, ABX type, H-7, H-7'), 4.904 (1H, d, $J_{5,4}$=2.0 Hz, H-5), 5.164 (1H, ddd, $J_{4,5}$=2.0, $J_{4,3}$=2.4, $J_{4,3'}$=9.4 Hz, H-4). HRMS (M+Cs$^+$) calcd C$_{13}$H$_{16}$O$_9$Cs 448.9849, found 448.9858.

Example 7

Methyl 2,4,5-tri-O-acetyl-2-keto-3-deoxy-α-L-gluconate (14)

13 (L-KDG): $^1$H NMR (D$_2$O) A major pair of H-3 protons: δ1.873 (dd, $J_{3eq,4}$=5.2, $J_{3eq,3ax}$=13.0 Hz, H-3eq), 1.984 (dd, $J_{3ax,4}$=11.9, $J_{3ax,3eq}$=13.0 Hz, H-3ax); a minor pair of H-3 protons: 2.051 (dd, $J_{3,4}$=3.2, $J_{3,3'}$=14.1 Hz, H-3), 2.521 (dd, $J_{3',4}$=7.5, $J_{3',3}$=14.1 Hz, H-3'); a minor H-3 proton ($^2$C$_5$ β-pyranose form is suggested): 2.167 (dd, $J_{3,4}$=4.0, $J_{3,3'}$=13.7 Hz), in this case the H-3' proton could not be specified by overlapping of the signals; another minor pair of H-3 protons: 2.284 (dd, J=6.4, 13.1 Hz), 2.341 (dd, J=6.4, 13.1 Hz); 3.60–4.10 (m), 4.15–4.20 (m), 4.30–4.40 (m).

14: (2.0 mg): $^1$H NMR (CDCl$_3$) δ2.034 (3H, s, acetyl), 2.150 (3H, s, acetyl), 2.152 (3H, s, acetyl), 2.288 (1H, d, $J_{3ax,4}$=10.1 Hz, H-3ax), 2.292 (1H, dd, $J_{3eq,5}$=0.4 Hz, $J_{3eq,4}$=7.0 Hz, H-3eq), 3.830 (3H, s, COOCH$_3$), 3.999 (1H, dd, $J_{6eq,5}$=1.5, $J_{6eq,6ax}$=13.2 Hz, H-6eq), 4.092 (1H, dd, $J_{6ax,5}$=2.0, $J_{6ax,6eq}$=13.2 Hz, H-6ax), 5.251 (1H, dddd, $J_{5,3eq}$=0.4, $J_{5,6eq}$=1.5 $J_{5,6ax}$=2.0, $J_{5,4}$=2.7 Hz, H-5), 5.313 (1H, ddd, $J_{4,5}$=2.7, $J_{4,3eq}$=7.0, $J_{4,3ax}$=10.1 Hz, H-4). HRMS (M+Na$^+$) calcd C$_{13}$H$_{18}$O$_9$Na 341.0849, found 341.0849.

Example 8

Methyl 2,4,5,7,8,9-hexa-O-acetyl-3-deoxy-β-L-glycero-L-galacto-nonulosonate (16)

15 (L-KDN): $^1$H NMR (D$_2$O) δ1.773 (1H, dd, $J_{3ax,4}$=11.8, $J_{3ax,3eq}$=12.9 Hz, H-3ax), 2.168 (1H, dd, $J_{3eq,4}$=5.1, $J_{3eq,3ax}$=11.8 Hz, H-3eq), 3.579 (1H, dd, $J_{5,4}$=9.3, $J_{5,6}$=9.9 Hz, H-5), 3.654 (1H, dd, $J_{9,8}$=6.3, $J_{9,9'}$=11.8 Hz, H-9), 3.766 (1H, ddd, $J_{8,9'}$=2.6, $J_{8,9}$=6.3, $J_{8,7}$=9.0 Hz, H-8), 3.831 (1H, dd, $J_{7,6}$=1.1, $J_{7,8}$=9.0 Hz, H-7), 3.873 (1H, dd, $J_{9',8}$=2.6, $J_{9',9}$=11.8 Hz, H-9'), 3.925 (1H, dd, $J_{6,7}$=1.1, $J_{6,5}$=9.9 Hz, H-6), 3.971 (1H, ddd, $J_{4,3eq}$=5.1, $J_{4,5}$=9.3, $J_{4,3ax}$=11.8 Hz, H-4).

16 (108.3 mg, 61% from 0.33 mmol of L-mannose): $[\alpha]^{25}$D +26.3° (c 1.14, CHCl$_3$); $^1$H NMR (CDCl$_3$) δ2.084 (1H, dd, $J_{3ax,4}$=11.6, $J_{3ax,3eq}$=13.6 Hz, H-3ax), 2.013 (3H, s, acetyl), 2.024 (3H, s, acetyl), 2.040 (3H, s, acetyl), 2.069 (3H, s, acetyl), 2.115 (3H, s, acetyl), 2.157 (3H, s, acetyl), 2.625 (1H, dd, $J_{3eq,4}$=5.3, $J_{3eq,3ax}$=13.6 Hz, H-3eq), 3.790 (3H, s, COOCH$_3$), 4.141 (1H, dd, $J_{9,8}$=5.8, $J_{9,9'}$=12.6 Hz, H-9), 4.186 (1H, dd, $J_{6,7}$=2.3, $J_{6,5}$=10.3 Hz, H-6), 4.440 (1H, dd, $J_{9',8}$=2.5, $J_{9',9}$=12.6 Hz, H-9'), 4.975 (1H, dd, $J_{5,4}$=9.6, $J_{5,6}$=10.3 Hz, H-5), 5.150 (1H, ddd, $J_{8,9}$=2.5, $J_{8,9'}$=5.8, $J_{8,7}$=6.3 Hz, H-8), 5.264 (1H, ddd, $J_{4,3eq}$=5.3, $J_{4,5}$=9.6, $J_{4,3ax}$=11.6 Hz, H-4), 5.396 (1H, dd, $J_{7,6}$=2.3, $J_{7,8}$=6.3 Hz, H-7); $^{13}$C NMR (CDCl$_3$) δ20.46, 20.48, 20.58, 20.58, 20.67, 35.32, 53.06, 61.67, 66.68, 67.21, 68.57, 70.00, 71.27, 97.14, 165.91, 168.03, 169.46, 169.57, 169.80, 169.96, 170.41. HRMS (M+Cs$^+$) calcd. C$_{22}$H$_{30}$O$_{15}$Cs 667.0639, found 667.0639.

16': $[\alpha]^{25}$D −26.0° (c 1.00, CHCl$_3$). The $^1$H NMR spectrum was identical with that of 16.

Example 9

2-Deoxy-2-fluoro-D-arabinose (17b)

To a solution of a tribenzoate 17a (available from Pfanstiehl Co., 500 mg, 1.08 mmol) in ethanol (5 mL) was added 10 N NaOH aqueous solution (485 μL, 1.5 eq of each OBz group, total 4.5 eq) at room temperature. After 15 min, H$_2$O (10 mL) and ethanol (5 mL) were added and the mixture was stirred and heated to 50° C. to dissolve the precipitated sodium benzoate. The mixture was further stirred for 1 h at room temperature. After ethanol was evaporated in vacuo, the residue was dissolved in H$_2$O and Dowex 50W-X8 (H$^+$ form) was added to acidify the mixture. The precipitated benzoic acid was filtered off, and the filtrate was treated with Dowex 1-X8 (HCO$_3^-$ form) and filtered, then concentrated in vacuo to give 17b as colorless syrup (153 mg, 94%); $^1$H NMR (D$_2$O) δ3.60–4.20 (4H, m), 4.337 (ddd, $J_{2,1}$=7.7, $J_{2,3}$=9.3, $J_{2,F}$=51.8 Hz, H-2 of β-anomer), 4.666 (ddd, $J_{2,1}$=3.7 $J_{2,3}$=9.5, $J_{2,F}$=49.5 Hz, H-2 of α-anomer), 4.763 (dd, $J_{1,F}$=3.3, $J_{1,2}$=7.7, H-1 of β-anomer), 5.434 (dd, $J_{1,F}$=1.5, $J_{1,2}$=3.7 Hz, H-1 of α-anomer). This anomeric mixture was used in the next step without further purification.

Example 10

Methyl 2,4,7,8-tetra-O-acetyl-3,5-dideoxy-5-fluoro-α-D-manno-2-octulosonate (19)

18: $^1$H NMR (D$_2$O) δ1.814 (dd, $J_{3ax,3eq}$=12.4, $J_{3ax,4}$=12.4 Hz, H-3ax of β-anomer), 1.988 (1H, ddd, $J_{3eq,5}$=0.8, $J_{3eq,4}$=5.6, $J_{3eq,3ax}$=12.9 Hz, H-3eq of α-anomer), 2.058 (1H, dd, $J_{3ax,4}$=11.8, $J_{3ax,3eq}$=12.9 Hz, H-3ax of α-anomer), 2.461 (ddd, $J_{3q,5}$=0.8 $J_{3eq,4}$=5.3, $J_{3eq,3ax}$=12.4 Hz, H-3eq of β-anomer), 3.663 (1H, dd, $J_{8,7}$=5.4, $J_{8,8'}$=12.1 Hz, H-8), 3.828 (1H, dd, $J_{8',7}$=2.4, $J_{8',8}$=12.1 Hz, H-8'), 3.80–3.95 (2H, m), 4.182 (1H, dddd, $J_{4,5}$=2.4, $J_{4,3eq}$=5.6, $J_{4,3ax}$=11.8, $J_{4,F}$=30.5 Hz, H-4), 4.957 (1H, ddd, $J_{5,3eq}$=0.8 $J_{5,4}$=2.4, $J_{5,F}$=50.9 Hz, H-5).

19 (25.3 mg, 18% from 0.33 mmol of 17b): $[\alpha]^{25}$D+96.4° (c 2.53, CHCl$_3$); $^1$H NMR (CDCl$_3$) δ2.043 (3H, s, acetyl), 2.067 (3H, s, acetyl), 2.131 (3H, s, acetyl), 2.137 (3H, s, acetyl), 2.271 (1H, dd, $J_{3ax,4}$=11.5, $J_{3ax,3eq}$=13.3 Hz, H-3ax), 2.319 (1H, dd, $J_{3eq,4}$=5.9, $J_{3eq,3ax}$=13.3 Hz, H-3eq), 3.805 (3H, s, COOCH$_3$), 4.073 (1H, dd, $J_{6,7}$=9.5, $J_{6,F}$=27.8 Hz, H-6), 4.154 (1H, dd, $J_{8,7}$=3.5, $J_{8,8'}$=12.5 Hz, H-8), 4.601 (1H, dd, $J_{8',7}$=2.2, $J_{8',8}$=12.5 Hz, H-8'), 4.827 (1H, dd, $J_{5,4}$=2.1, $J_{5,F}$=50.9 Hz, H-5), 5.240 (1H, dddd, $J_{4,5}$=2.1, $J_{4,3eq}$=5.9, $J_{4,3ax}$=11.5, $J_{4,F}$=21.3 Hz, H-4), 5.288 (1H, ddd, $J_{7,8'}$=2.2, $J_{7,8}$=3.5, $J_{7,6}$=9.5 Hz, H-7); $^{13}$C NMR (CDCl$_3$) δ20.56, 20.56, 20.71, 20.83, 30.60, 53.18, 61.46, 66.45, (d, $J_{C,F}$=17.8 Hz), 67.89 (d, $J_{C,F}$=4.1 Hz), 69.60 (d, $J_{C,F}$=18.2 Hz), 83.02 (d, $J_{C,F}$=186.2 Hz), 97.04, 166.49, 167.75, 169.14, 170.18, 170.20. HRMS (M+Cs$^+$) calcd C$_{17}$H$_{23}$O$_{11}$FCs 555.0279, found 555.0288.

Example 11

Larger Scale Synthesis of 18

Fluorosugar 17b (340 mg, 2.25 mmol), sodium pyruvate (2.074 g, 28.9 mmol), dithiothreitol (1.7 mg), NaN$_3$ (2.3 mg), phosphate buffer (pH 7.5, 50 mM, 1.12 mL) was added to the enzyme solution (3.0 mL, 24 U). After the pH was adjusted to 7.5, the volume was made up to 10.0 mL. The mixture was stirred under N$_2$ at room temperature for 7 days. The pH was lowered to 2.5 by addition of Dowex 50W-X8 (H$^+$ form) and the mixture was kept at 0° C. for 1 h. The precipitate was removed by centrifugation at 23,000×g for 1 h at 4° C. Before the anion-exchange resin treatment, the excess pyruvate was removed as follows. The mixture was diluted to 80 mL and the pH was adjusted to 6.5 by the addition of 2N aqueous ammonia solution. The antifoam (Antifoam AF emulsion, Dow—Corning Nakaraitesque, 10% emulsion in water, 0.32 mL) and pyruvate decarboxylase (Sigma P 6810, 0.2 mL, 12.5 U) was added and the mixture was stirred at room temperature with bubbling of N$_2$ (1.5 L/min). The pH was monitored and occasionally adjusted between 6.0 and 6.5, by addition of Dowex 50W-X8 (H$^+$ form). The decarboxylase was periodically added to the mixture (each 0.2 mL) at an interval of 30 min, to avoid the denaturation which is caused by the rapid formation of acetaldehyde. The total amount of the enzyme was 3.2 mL (200 U). The reaction mixture was further stirred overnight. Then the mixture was centrifuged, and the supernatant was diluted to 100 mL and applied to a column of Dowex 1-X8 (20–50 mesh, bicarbonate form, bed volume, 100 mL). The pH of the eluent and washings was re-adjusted to 5.5 and further applied to the same column to ensure the adsorption of desired product. After washing with water, the desired product was eluted with a linear gradient from 0 to 0.3 M of ammonium bicarbonate. The product was further purified by Biogel P-2 column (bed volume 20 mL) to give 192 mg (33i) of 18. The $^1$H NMR spectrum was identical with the sample mentioned above.

Example 12

Benzyl 2,4,5,7,8-pneta-O-acetyl-3-deoxy-α-D-manno-2-octulosonate (20b)

A suspension of KDO ammonium salt monohydrate (160 mg, 0.59 mmol), acetic anhydride (3 mL), pyridine (3 mL), and 4-(N,N-dimethylamino)pyridine (DMAP, 2 mg) was stirred overnight at room temperature. Ice-cooled water was added and the mixture was stirred for 30 min. After dilution with water, the pH of the mixture was adjusted to 3.5 by addition of Dowex 50W-X8 ($H^+$ form). The resin was filtered off, and the filtrate was concentrated in vacuo. The residue was diluted with a mixture of chloroform and toluene and the solvent was evaporated. This procedure was repeated three times to remove trace of water. The residue was dissolved in anhydrous DMF. Benzyl bromide (161 mg, 0.94. mmol), $Cs_2CO_3$ (390 mg, 1.20 mmol), and tetrabutylammonium iodide (33 mg) were added and the mixture was stirred for 4 h at room temperature under $N_2$. The mixture was diluted with 0.5 N ice-cooled hydrochloric acid and extracted twice with a mixture of diethyl ether and toluene (1:1). The organic layer was successively washed with water, saturated aqueous $NaHCO_3$ and brine, dried over anhydrous $Na_2SO_4$ and concentrated in vacuo. The residue was chromatographed over silica gel (20 g). Elution with hexane-diethyl ether (2:1-1:1) afforded 15b, which was recrystallized from diethyl ether to give 220 mg (70%) as colorless plates, mp 102–103° C. (lit.[26b] mp 98–99° C.); $[\alpha]^{26}D+293°$ (c 1.0, $CHCl_3$) [lit.[26b] $[\alpha]^{25}D+91.9°$ (c 0.9, $CHCl_3$). Its $^1H$ NMR spectrum ($CDCl_3$) was in good accordance with that reported previously by Nakamoto (*Chem. Pharm. Bull.* 1987, 35, 4537). HRMS ($M+Na^+$) calcd 561.1584, found 561.1602.

Example 13

2,4,5,7,8-Penta-O-acetyl-3-deoxy-α-D-manno-2-octulosonic acid (20a)

A mixture of 20b (220 mg, 0.41 mmol) and Pd—C (10%, 55 mg) in ethanol (3 mL) was vigorously stirred under $H_2$ at room temperature for 1 h. After the catalyst was filtered off, the filtrate was concentrated in vacuo. The residue was recrystallized from diethyl ether to give 20a (177 mg, 97%) as fine needles, mp 132–133° C.; $[\alpha]^{25}D+374°$ (c 0.88, $CHCl_3$). Its $^1H$ NMR spectrum ($C_6D_6$) was identical with that reported previously by Unger et al. (*Carbohydr. Res.* 1980, 80, 191).

Example 14

1,3,4,6,7-Penta-O-acetyl-2-deoxy-β-D-manno-heptose (21)

To a solution of acid chloride prepared from 20a (30 mg, 0.067 mmol) in toluene was added dropwise a solution of N-hydroxythiopyridone 22 (11 mg, 0.09 mmol) and DMAP (2 mg) in toluene (0.5 mL) and pyridine (0.3 mL) at room temperature under $N_2$ in the dark. After stirring for 10 min, t-butylmercaptane (0.5 mL) was added and the mixture was irradiated with white light (tungsten lamp, 100 W) at room temperature. After stirring for 10 min, $N_2$ was introduced to the mixture under a slightly reduced pressure to remove residual t-butylmercaptane for 30 min. Usual workup and purification by silica gel preparative TLC [developed with hexane-$Et_2O$ (1:1)] afforded 21 (18.5 mg, 68%) as an oil, $[\alpha]^{22}D+36.8°$ (c 1.85, $CHCl_3$); $^1H$ NMR ($CDCl_3$) δ2.000–2.150 (2H, m, H-2ax, H-2eq), 2.010 (6H, s, acetyl), 2.082 (3H, s, acetyl), 2.119 (3H, s, acetyl), 2.137 (3H, s, acetyl), 3.882 (1H, dd, $J_{5,4}$=1.5, $J_{5,6}$=10.0 Hz, H-5), 4.115 (1H, dd, $J_{7',6}$=4.5, $J_{7',7}$=12.5 H, H-7'), 4.437 (1H, dd $J_{7,6}$=2.5, $J_{7,7'}$=12.5 Hz, H-7), 5.073 (1H, ddd, $J_{3,4}$=3.0, $J_{3,2eq}$=5.0, $J_{3,2ax}$=12.5 Hz, H-3), 5.165 (1H, ddd, $J_{6,7}$=2.5, $J_{6,7'}$=4.5, $J_{6,5}$=10.0 Hz, H-6), 5.303 (1H ,dd, $J_{4,5}$=1.5, $J_{4,3}$=3.0 Hz, H-4), 5.748 (1H, dd, $J_{1,2eq}$=3.0, $J_{1,2ax}$=10.0 Hz, H-1); $^{13}C$ NMR ($CDCl_3$) δ20.59, 20.59, 20.65, 20.65, 20.84, 30.35, 62.26, 63.84, 67.32, 67.90, 71.62, 91.67, 168.60, 169.60, 169.83, 170.30, 170.54. HRMS ($M+Cs^+$) calcd $C_{17}H_{24}O_{11}Cs$ 537.0373, found 537.0359.

Example 15

4-Acetamdo-1,3,6,7,8-Penta-O-acetyl-2,4-dideoxy-α-D-glycero-D-galacto-octose (24)

A 25 mL two-necked flask equipped with septum, microscale Dean-Stark trapp which was filled with molecular sieves 4A, and a reflux condenser, was used as the reaction vessel. A mixture of 23a (35.0 mg, 0.07 mmol), DMAP (12.3 mg, 1.5 eq), 22 (41.0 mg, 5.0 eq), triethylamine (19 μL) in $CH_2Cl_2$ (1 mL) was placed in the flask as above. To this was successively added a solution of WSCI-Cl (20 mg) in $CH_2Cl_2$(1 mL) and t-butylmercaptane (0.5 mL). The mixture was stirred and irradiated with white light (tungsten lamp, 100 W) at room temperature for 5 h. The reaction was worked up in a similar manner as described above. The crude product was purified by silica gel preparative TLC [developed with ethyl acetate-tetrahydrofuran (1:1)] to give 24 (8.7 mg, 27% from 23a) as an oil, $[\alpha]^{22}D+21.3°$ (c 2.87, $CHCl_3$); $^1H$ NMR ($CDCl_3$) δ1.908 (3H, s, N-acetyl), 1.915 (1H, ddd, $J_{2ax,1}$=10.3, $J_{2ax,3}$=11.5, $J_{2ax,2eq}$=12.4 Hz, H-2ax), 2.043 (3H, s, O-acetyl), 2.051 (3H, s, O-acetyl), 2.102 (3H, s, O-acetyl), 2.107 (3H, s, O-acetyl), 2.134 (3H, s, O-acetyl), 2.219 (1H, ddd, $J_{2eq,1}$=2.1, $J_{2eq,3}$=4.9, $J_{2eq,2ax}$=12.4 Hz, H-2eq), 3.764 (1H, dd, $J_{5,6}$=2.4, $J_{5,4}$=10.4 Hz, H-5), 4.023 (1H, dd, $J_{8,7}$=5.5, $J_{8,8'}$=12.6 Hz, H-8), 4.062 (1H, ddd, $J_{4,NH}$=10.0, $J_{4,3}$=10.3, $J_{4,5}$=10.4 Hz, H-4), 4.389 (1H, ddd, $J_{8'7}$=2.6, $J_{8',8}$=12.6 Hz, H-8'), 5.127 (1H, ddd, $J_{7,8'}$=2.6, $J_{7,8}$=5.5, $J_{7,6}$=7.3 Hz, H-7), 5.058 (1H, ddd, $J_{3,2eq}$=4.9, $J_{3,4}$=10.3, $J_{3,2ax}$=11.5 Hz, H-3) 5.190 (1H, d, $J_{NH,4}$=10.0 Hz, NH), 5.391 (1H, dd, $J_{6,7}$=7.3, $J_{6,5}$=2.4 Hz, H-6), 5.646 (1H, dd, $J_{1,2eq}$=2.1, $J_{1,2ax}$=10.3 Hz, H-1); $^{13}C$ NMR ($CDCl_3$) δ20.70, 20.70, 20.75, 20.83, 20.83, 23.15, 35.09, 49.22, 61.98, 67.11, 70.23, 70.23, 73.67, 91.19, 168.75, 169.90, 170.12, 170.36, 170.59, 170.88. HRMS ($M+Cs^+$) calcd $C_{20}H_{29}O_{12}NCs$ 608.0744, found 608.0750.

What is claimed is:

1. A method of synthesizing a 7–8 carbon 2-deoxy-aldose comprising the following steps:

Step A: providing a protected form of 8–9 carbon 2-keto-3-deoxy-onic acid with protected side groups exclusive of the acid group; then Step B: condensing the acid group of the 8–9 carbon 2-keto-3-deoxy-onic acid of said Step A with a thiohydroxamic acid to a form an O-acyl thiohydroxamate intermediate; then Step C: decarboxylating the O-acyl thiohydroxamate intermediate of said Step B by means of a radical mediated decarboxylation for forming a protected form of the 7–8 carbon 2-deoxy-aldose; and then Step D: deprotecting the protected form of the 7–8 carbon 2-deoxy-aldose of said Step C for forming the 7–8 carbon 2-deoxy-aldose.

2. A method according to claim 1 wherein the 7–8 carbon 2-deoxy-aldose is 2-deoxy-β-D-manno-heptose and wherein:

in said Steps A and B, the protected 8–9 carbon 2-keto-3-deoxy-onic acid is 2,4,5,7,8-penta-O-acetyl-3-deoxy-α-D-manno-2-octoulosonic acid.

3. A mehtod according to claim 2 wherein the 7–8 carbon 2-deoxy-aldose is 4-amido-2,4-dideoxy-β-D-glycero-D-galacto-octose and wherein:

in said Steps A and B, the protected 8–9 carbon 2-keto-3-deoxy-onic acid is 4-acetamido-1,3,6,7,8-penta-O-acetyl-2,4-dedeoxy-α-D-glycero-D-D-galacto-octose.

4. A method of synthesizing a 7–8 carbon 2-deoxy-aldose according to claim 1 wherein:

in said Step B, the thiohydroxamic acid is 2-mercaptopyridine N-oxide.

5. A method of synthesizing a 7–8 carbon 2-deoxy-aldose according to claim 4 wherein:

in said Step C, the radical mediated decarboxylation is effected by irradiation with light.

* * * * *